(12) United States Patent  
Nguyen et al.

(10) Patent No.: US 8,900,370 B2  
(45) Date of Patent: **\*Dec. 2, 2014**

(54) METHOD AND APPARATUS FOR CONVEYING A CELLULOSIC FEEDSTOCK

(75) Inventors: Quang A. Nguyen, Chesterfield, MO (US); Sunalie N. Hillier, Georgetown (CA); Murray J. Burke, Oakville (CA)

(73) Assignee: Abengoa Bioenergy New Technologies, LLC., Chesterfield, MO (US)

( * ) Notice: Subject to any disclaimer, the term of this patent is extended or adjusted under 35 U.S.C. 154(b) by 1243 days.

This patent is subject to a terminal disclaimer.

(21) Appl. No.: 12/181,565

(22) Filed: Jul. 29, 2008

(65) Prior Publication Data

US 2010/0024806 A1 Feb. 4, 2010

(30) Foreign Application Priority Data

Jul. 24, 2008 (CA) ...................................... 2638150

(51) Int. Cl.
| | |
|---|---|
| *C13K 13/00* | (2006.01) |
| *C13K 1/02* | (2006.01) |
| *B01F 3/20* | (2006.01) |
| *B01F 5/00* | (2006.01) |

(52) U.S. Cl.  
CPC ... *C13K 1/02* (2013.01); *B01F 5/00* (2013.01); *Y02E 50/16* (2013.01); *C13K 13/00* (2013.01); *B01F 3/20* (2013.01)  
USPC .................. 127/37; 127/1; 366/145; 366/147; 366/149; 366/153.3; 366/167.1

(58) Field of Classification Search  
CPC ............ C13K 13/00; C13K 1/02; B01F 3/20; B01F 5/00; Y02E 50/16  
USPC .................. 34/329, 343, 357, 363; 127/1, 37; 198/657; 366/145, 147, 149, 153.3, 366/167.1; 406/53, 55  
See application file for complete search history.

(56) References Cited

U.S. PATENT DOCUMENTS

| | | | |
|---|---|---|---|
| 319,299 | A | 6/1885 | Morgan |
| 459,113 | A | 9/1891 | Rymal |

(Continued)

FOREIGN PATENT DOCUMENTS

| | | |
|---|---|---|
| CA | 1070537 | 1/1980 |
| CA | 1096374 B | 2/1981 |

(Continued)

OTHER PUBLICATIONS

International Search Report and the Written Opinion received on the corresponding PCT Application No. PCT/CA2009/001036, dated Nov. 13, 2009.

(Continued)

*Primary Examiner* — David A Reifsnyder  
(74) *Attorney, Agent, or Firm* — Armstrong Teasdale LLP.

(57) ABSTRACT

A method and apparatus for preparing a cellulosic feedstock are disclosed. Embodiments of the method comprise obtaining a cellulosic feedstock having a moisture content of 30 wt % to 60 wt %; passing the cellulosic feedstock through a heated holding tank; withdrawing the cellulosic feedstock from the holding tank; and, subsequently subjecting the cellulosic feedstock to hydrolysis. Embodiments of the apparatus comprise at least one sidewall defining a volume having an upper portion and a lower portion. At least one inlet is provided adjacent the upper portion, and the inlet is in fluid communication with an impregnation chamber provided upstream from the holding tank. At least one outlet is provided adjacent the lower portion, and the outlet is in fluid communication with hydrolysis reactor positioned downstream from the holding tank. At least one conveyor is positioned adjacent the at least one outlet. A heating jacket provided on at least a portion of the apparatus.

22 Claims, 10 Drawing Sheets

(56) References Cited

U.S. PATENT DOCUMENTS

| | | |
|---|---|---|
| 1,073,425 A | 9/1913 | Lambert |
| 1,106,736 A | 8/1914 | Schuller |
| 1,173,825 A | 2/1916 | McWallen |
| 1,190,923 A | 7/1916 | Lindquist |
| 1,247,153 A | 11/1917 | Roberts |
| 1,560,855 A | 11/1925 | Queneau |
| 1,824,221 A | 9/1931 | Mason |
| 2,080,327 A | 5/1937 | McKinnis |
| 2,086,701 A | 7/1937 | Dreyfus |
| 2,263,608 A | 11/1941 | Brown |
| 2,333,730 A | 11/1943 | Puckett |
| 2,541,058 A | 2/1951 | Heritage et al. |
| 2,541,059 A | 2/1951 | Heritage et al. |
| 2,541,127 A | 2/1951 | Van Beckum |
| 2,570,042 A | 10/1951 | West |
| 2,595,827 A | 5/1952 | Boruff et al. |
| 2,615,883 A | 10/1952 | Sweeney et al. |
| 2,697,703 A | 12/1954 | Heritage et al. |
| 2,758,031 A | 8/1956 | Ozai-Durrani |
| 3,017,404 A | 1/1962 | Ball |
| 3,109,560 A | 11/1963 | Rosenleaf |
| 3,199,731 A | 8/1965 | Brauer et al. |
| 3,223,697 A | 12/1965 | Ball et al. |
| 3,357,437 A | 12/1967 | Maguire |
| 3,383,277 A | 5/1968 | Gordon et al. |
| 3,407,943 A | 10/1968 | Douglass, Jr. |
| 3,572,593 A | 3/1971 | Guarisco |
| 3,617,433 A | 11/1971 | Sutherland |
| 3,640,509 A | 2/1972 | Inamura et al. |
| 3,743,572 A | 7/1973 | Richter et al. |
| 3,817,826 A | 6/1974 | Hoye |
| 3,964,874 A | 6/1976 | Maruko et al. |
| 3,964,880 A | 6/1976 | Siegrist |
| 4,023,982 A | 5/1977 | Knauth |
| 4,055,673 A | 10/1977 | Mueller et al. |
| 4,062,304 A | 12/1977 | Herbold et al. |
| 4,119,025 A | 10/1978 | Brown |
| 4,136,207 A | 1/1979 | Bender |
| 4,160,695 A | 7/1979 | Dietrichs et al. |
| 4,181,796 A | 1/1980 | Dietrichs et al. |
| 4,186,658 A | 2/1980 | Brown |
| 4,196,827 A | 4/1980 | Leafdale |
| 4,200,692 A | 4/1980 | Puls et al. |
| 4,211,163 A | 7/1980 | Brown et al. |
| 4,237,226 A | 12/1980 | Grethlein |
| 4,281,934 A | 8/1981 | Krause et al. |
| 4,286,884 A | 9/1981 | Retrum |
| 4,296,864 A | 10/1981 | Misaka et al. |
| 4,316,748 A | 2/1982 | Rugg et al. |
| 4,331,447 A | 5/1982 | Kamada et al. |
| 4,341,353 A | 7/1982 | Hamilton et al. |
| 4,364,667 A | 12/1982 | Reiner |
| 4,412,485 A | 11/1983 | Brown |
| 4,427,453 A | 1/1984 | Reitter |
| 4,432,805 A | 2/1984 | Nuuttila et al. |
| 4,436,586 A | 3/1984 | Elmore |
| 4,451,567 A | 5/1984 | Ishibashi et al. |
| 4,461,648 A | 7/1984 | Foody |
| 4,470,851 A | 9/1984 | Paszner et al. |
| 4,483,625 A | 11/1984 | Fisher |
| 4,511,433 A | 4/1985 | Tournier et al. |
| 4,584,057 A | 4/1986 | Rowe et al. |
| 4,600,590 A | 7/1986 | Dale |
| 4,615,742 A | 10/1986 | Wright |
| 4,645,541 A | 2/1987 | DeLong |
| 4,667,373 A | 5/1987 | Roder |
| 4,670,944 A | 6/1987 | Thrash |
| 4,676,363 A | 6/1987 | Buchmuller et al. |
| 4,746,404 A | 5/1988 | Laakso |
| 4,751,034 A | 6/1988 | DeLong et al. |
| 4,752,579 A | 6/1988 | Arena et al. |
| 4,764,596 A | 8/1988 | Lora et al. |
| 4,775,239 A | 10/1988 | Martinek et al. |
| 4,798,651 A | 1/1989 | Kokta |
| 4,867,846 A | 9/1989 | Fleck |
| 4,869,786 A | 9/1989 | Hanke |
| 4,908,098 A | 3/1990 | DeLong et al. |
| 4,908,099 A | 3/1990 | DeLong |
| 4,911,558 A | 3/1990 | Teske |
| 4,947,743 A | 8/1990 | Brown et al. |
| 4,966,650 A | 10/1990 | DeLong et al. |
| 4,997,488 A | 3/1991 | Gould et al. |
| 5,012,731 A | 5/1991 | Maisonneuve |
| 5,023,097 A | 6/1991 | Tyson et al. |
| 5,034,099 A | 7/1991 | Nilsson |
| 5,047,332 A | 9/1991 | Chahal |
| 5,052,874 A | 10/1991 | Johanson |
| 5,100,066 A | 3/1992 | Frei |
| 5,114,488 A | 5/1992 | Huber et al. |
| 5,122,228 A | 6/1992 | Bouchette et al. |
| 5,135,861 A | 8/1992 | Pavilon |
| 5,176,295 A | 1/1993 | Stefanik |
| 5,181,804 A | 1/1993 | Wysong et al. |
| 5,188,298 A | 2/1993 | Gerber |
| 5,198,074 A | 3/1993 | Villavicencio et al. |
| 5,221,357 A | 6/1993 | Brink |
| 5,338,366 A | 8/1994 | Grace et al. |
| 5,348,871 A | 9/1994 | Scott et al. |
| 5,366,558 A | 11/1994 | Brink |
| 5,411,594 A | 5/1995 | Brelsford |
| 5,417,492 A | 5/1995 | Christian et al. |
| 5,424,417 A | 6/1995 | Torget et al. |
| 5,487,989 A | 1/1996 | Fowler et al. |
| 5,503,996 A | 4/1996 | Torget et al. |
| 5,504,259 A | 4/1996 | Diebold et al. |
| 5,536,325 A | 7/1996 | Brink |
| 5,571,703 A | 11/1996 | Chieffalo et al. |
| 5,597,714 A | 1/1997 | Farone et al. |
| 5,611,930 A | 3/1997 | Nguyen et al. |
| 5,628,830 A | 5/1997 | Brink |
| 5,677,154 A | 10/1997 | Van Draanen et al. |
| 5,705,213 A | 1/1998 | Tyson |
| 5,705,369 A | 1/1998 | Torget et al. |
| 5,730,837 A | 3/1998 | Black et al. |
| 5,733,758 A | 3/1998 | Nguyen |
| 5,735,916 A | 4/1998 | Lucas et al. |
| 5,791,779 A | 8/1998 | Smith |
| 5,843,760 A | 12/1998 | Zhang et al. |
| 5,863,389 A | 1/1999 | White et al. |
| 5,916,780 A | 6/1999 | Foody et al. |
| 5,932,452 A | 8/1999 | Mustranta et al. |
| 6,022,419 A | 2/2000 | Torget et al. |
| 6,063,204 A | 5/2000 | Hester et al. |
| 6,090,595 A | 7/2000 | Foody et al. |
| 6,199,299 B1 | 3/2001 | Prough et al. |
| 6,228,177 B1 | 5/2001 | Torget |
| 6,330,767 B1 | 12/2001 | Carr et al. |
| 6,336,573 B1 | 1/2002 | Johanson |
| 6,409,841 B1 | 6/2002 | Lombard |
| 6,419,788 B1 | 7/2002 | Wingerson |
| 6,423,145 B1 | 7/2002 | Nguyen et al. |
| 6,498,029 B2 | 12/2002 | Keller, Jr. et al. |
| 6,557,267 B2 | 5/2003 | Wanger |
| 6,569,653 B1 | 5/2003 | Alard et al. |
| 6,572,734 B2 | 6/2003 | Baker |
| 6,620,292 B2 | 9/2003 | Wingerson |
| 6,648,251 B1 | 11/2003 | Chollet |
| 6,660,506 B2 | 12/2003 | Nguyen et al. |
| 6,737,258 B2 | 5/2004 | Hames et al. |
| 6,743,928 B1 | 6/2004 | Zeitsch |
| 6,908,995 B2 | 6/2005 | Blount |
| 6,927,048 B2 | 8/2005 | Verser et al. |
| 7,109,005 B2 | 9/2006 | Eroma et al. |
| 7,178,698 B2 | 2/2007 | Forslund et al. |
| 7,198,925 B2 | 4/2007 | Foody |
| 7,238,242 B2 | 7/2007 | Pinatti et al. |
| 7,396,434 B2 | 7/2008 | Rodriguez Rivera et al. |
| 7,445,691 B2 | 11/2008 | Snekkenes et al. |
| 7,461,591 B2 | 12/2008 | Babbini |
| 7,494,675 B2 | 2/2009 | Abbas et al. |
| 7,503,981 B2 | 3/2009 | Wyman et al. |
| 7,875,444 B2 | 1/2011 | Yang et al. |
| 7,901,511 B2 | 3/2011 | Griffin et al. |
| 7,937,851 B2 * | 5/2011 | Rajagopalan et al. .......... 34/357 |

(56) References Cited

U.S. PATENT DOCUMENTS

| | | | |
|---|---|---|---|
| 7,993,463 B2 | 8/2011 | Griffin et al. | |
| 8,051,986 B2 | 11/2011 | Lees | |
| 8,053,566 B2 | 11/2011 | Belanger et al. | |
| 8,193,395 B2 | 6/2012 | Fenton et al. | |
| 8,449,680 B2 | 5/2013 | Burke et al. | |
| 2002/0003032 A1 | 1/2002 | Nay et al. | |
| 2002/0164731 A1 | 11/2002 | Eroma et al. | |
| 2003/0089465 A1 | 5/2003 | Schaible et al. | |
| 2004/0121436 A1 | 6/2004 | Blount | |
| 2004/0154760 A1 | 8/2004 | Dean | |
| 2004/0171136 A1 | 9/2004 | Holtzapple et al. | |
| 2004/0231661 A1 | 11/2004 | Griffin et al. | |
| 2004/0231811 A1 | 11/2004 | Engstrand et al. | |
| 2005/0269048 A1 | 12/2005 | Rodriguez et al. | |
| 2006/0088922 A1 | 4/2006 | Yang et al. | |
| 2006/0163118 A1 | 7/2006 | Kelsey et al. | |
| 2006/0169430 A1 | 8/2006 | Tarasenko | |
| 2006/0188965 A1 | 8/2006 | Wyman et al. | |
| 2006/0233864 A1 | 10/2006 | Power | |
| 2006/0272518 A1 | 12/2006 | Babbini | |
| 2006/0275895 A1* | 12/2006 | Jensen et al. | 435/300.1 |
| 2007/0037267 A1 | 2/2007 | Lewis et al. | |
| 2007/0148751 A1 | 6/2007 | Griffin et al. | |
| 2007/0209974 A1 | 9/2007 | Lees | |
| 2007/0215300 A1 | 9/2007 | Upfal et al. | |
| 2007/0218530 A1 | 9/2007 | Duck et al. | |
| 2007/0227063 A1 | 10/2007 | Dale et al. | |
| 2008/0026431 A1 | 1/2008 | Saito et al. | |
| 2008/0038784 A1 | 2/2008 | D'Arnaud-Taylor | |
| 2008/0227161 A1 | 9/2008 | Levie et al. | |
| 2009/0029432 A1 | 1/2009 | Abbas et al. | |
| 2009/0062516 A1 | 3/2009 | Belanger et al. | |
| 2009/0069550 A1 | 3/2009 | Belanger et al. | |
| 2009/0098616 A1 | 4/2009 | Burke et al. | |
| 2009/0098617 A1 | 4/2009 | Burke et al. | |
| 2009/0240088 A1 | 9/2009 | Fenton et al. | |
| 2009/0246848 A1 | 10/2009 | Noel | |
| 2010/0024807 A1* | 2/2010 | Burke et al. | 127/1 |
| 2010/0024808 A1* | 2/2010 | Burke et al. | 127/37 |
| 2010/0024809 A1* | 2/2010 | Burke et al. | 127/1 |
| 2010/0028089 A1* | 2/2010 | Burke et al. | 406/53 |
| 2010/0124583 A1 | 5/2010 | Medoff | |
| 2010/0186735 A1* | 7/2010 | Burke et al. | 127/1 |
| 2010/0186736 A1* | 7/2010 | Burke et al. | 127/1 |
| 2011/0011391 A1* | 1/2011 | Burke | 127/1 |
| 2012/0111321 A1* | 5/2012 | Nguyen et al. | 127/37 |

FOREIGN PATENT DOCUMENTS

| | | |
|---|---|---|
| CA | 1147105 A | 5/1983 |
| CA | 1173825 A1 | 9/1984 |
| CA | 1190923 A1 | 7/1985 |
| CA | 1267407 | 3/1990 |
| CA | 1287705 | 8/1991 |
| CA | 2037275 A1 | 8/1992 |
| CA | 1322366 C | 9/1993 |
| CA | 2063547 A1 | 9/1993 |
| CA | 2065939 A1 | 10/1993 |
| CA | 2339002 A1 | 7/1999 |
| CA | 2638150 A1 | 1/2010 |
| CA | 2638159 | 1/2010 |
| CN | 200981760 | 11/2007 |
| EP | 0487793 A1 | 6/1992 |
| EP | 1036236 | 9/1998 |
| EP | 0884391 B1 | 1/2002 |
| EP | 1316620 A2 | 6/2003 |
| FR | 777824 | 3/1935 |
| GB | 892506 | 3/1957 |
| GB | 1043460 A | 9/1966 |
| WO | 9213849 A1 | 8/1992 |
| WO | 2005079190 A2 | 9/1995 |
| WO | 9640970 A1 | 12/1996 |
| WO | 9732073 A1 | 9/1997 |
| WO | 0238787 A2 | 5/2002 |
| WO | 2004018645 A2 | 3/2004 |
| WO | 2004081193 A2 | 9/2004 |
| WO | 2004106624 A1 | 12/2004 |
| WO | 2005118165 A1 | 12/2005 |
| WO | 2006017655 A3 | 2/2006 |
| WO | 2006034591 A1 | 4/2006 |
| WO | 2006055362 A1 | 5/2006 |
| WO | 2006-063467 | 6/2006 |
| WO | 2007009463 A2 | 1/2007 |
| WO | 2007064296 A1 | 6/2007 |
| WO | 2007065241 A1 | 6/2007 |
| WO | 2007111605 A1 | 10/2007 |
| WO | 2008086115 A2 | 7/2008 |
| WO | 2008144903 A1 | 12/2008 |
| WO | 2009012779 | 1/2009 |
| WO | 2009018469 A1 | 2/2009 |
| WO | 2009089439 A1 | 7/2009 |
| WO | 2010006840 A2 | 1/2010 |
| WO | 2010009547 A1 | 1/2010 |
| WO | 2010009548 A1 | 1/2010 |
| WO | 2010009550 A1 | 1/2010 |
| WO | WO 2010009551 A1 * | 1/2010 |
| WO | 2010083600 A1 | 7/2010 |
| WO | 2010083601 | 7/2010 |
| WO | 2010009549 | 1/2011 |
| WO | 2011028554 A1 | 3/2011 |

OTHER PUBLICATIONS

Brownell et al.: "Steam-Explosion Pretreatment of Wood: Effect of Chip Size, Acid, Moisture Content and Pressure Drop", Biotechnology and Bioengineering, vol. 28, pp. 792-801, (1986).

Cullis et al.: Effect of Initial Moisture Content and Chip Size on the Bioconversion Efficiency of Softwood Lignocellulosics:, Biotechnology and Bioengineering, vol. 85, No. 4, pp. 413-421, (2004).

Duff et al.: "Bioconversion of forest products industry waste cellulosics to fuel ethanol; A review", Bioresource Technology, vol. 5, pp. 1-33 (1996).

Q.A. Nguyen et al., "NREL/DOE Ethanol Pilot-Plant: Current Status and Capabilities" (1996) 58 Bioresource Technology 189.

R.P. Overend & E. Chornet, "Fractionation of lignocellulosics by steam-aqueous pretreatments" (1987) 321 Phil. Trans. R. Soc. Lond. A. 523.

D. Ballerini et al., "Ethanol Production from Lignocellulosics: Large Scale Experimentation and Economics" (1994) 50 Biousource Technology 17.

K.M.F. Kazi, P. Jollez, & E. Chornet, "Preimpregnation: An Important Step for Biomass Refining Processes" (1998) 15:2 Biomass and Bioenergy 125.

M.P. Tucker et al., "Comparison of Yellow Poplar Pretreatment Between NREL Digester and Sunds Hydrolyzer" (1998) 70-72 Applied Biochemistry and Biotechnology 25.

Charles E. Wyman et al., "Comparative Sugar Recovery Data from Laboratory Scale Application of Leading Pretreatment Technologies to Corn Stover" (2005) 96 Bioresource Technology 2026.

Charles E. Wyman et al., "Coordinated Development of Leading Biomass Pretreatment Technologies" (2005) 96 Bioresource Technology 1959.

Nathan Mosier et al., "Features of Promising Technologies for Pretreatment of Lignocellulosic Biomass" (2005) 96 Biosource Technology 673.

Tim Eggeman & Richard T. Elander, "Process and Economics Analysis of Pretreatment Technologies" (2005) 96 Bioresource Technology 2019.

Abengoa Bioenergy, Press Release, "Abengoa Bionergy Awarded DOE Financial Assistance Agreement" (Feb. 28, 2007), online: Abongoa Bioenergy <http://www.abengoabioenergy.es/corp/web/en/acerca_de/sala_de_prensa/historico/2007/20070228_noticias.html#>.

Outputs from the EPOBIO Workshop, Greece, "Products from Plants—From Crops and Forests to Zero Waste Biorefineries" (May 15-17, 2007).

Abengoa Bioenergy, Press Release, "Abengoa Bionergy Opens Pilot Plant for the Energy of the Future" (Oct. 15, 2007), online: Abengoa

(56) References Cited

OTHER PUBLICATIONS

Bioenergy <http://www.abengoabioenergy.es/corp/web/en/acerca_de/sala_de_prensa/historico/2007/20071015_noticias.html#>.

Merrick & Company, Final Report of Jun. 14, 1999, "Softwood Biomass to Ethanol Feasibility Study" (Aug. 2004) Subcontractor Report published by National Renewable Energy Laboratory.

Merrick & Company, Final Report of Jan. 2000, "Building a Bridge to the Corn Ethanol Industry. Corn Stover to Ethanol at High Plains Corporation's York, Nebraska Co-Located Plant Site".

Melvin P. Tucker et al., "Conversion of Distiller's Grain into Fuel Alcohol and a Higher-Value Animal Feed by Dilute-Acid Pretreament" (2004) 113-116 Applied Biochemistry and Biotechnology 1139.

Melvin P. Tucker et al., "Effects of Temperature and Moisture on Dilute-Acid Steam Explosion Pretreatment of Corn Stover and Cellulase Enzyme Digestibility" (2003) 105-108 Applied Biochemistry and Biotechnology 165.

Kyoung Heon Kim et al., "Continuous Countercurrent Extraction of Hemicellulose from Pretreated Wood Residues" (2001) 91-93 Applied Biochemistry and Biotechnology 253.

Quang A. Nguyen et al., "Two-Stage Diute-Acid Pretreatment of Softwoods" (2000) 84-86 Applied Biochemistry and Biotechnology 561.

Daniel J. Schell et al., "Dilute-Sulfuric Acid Pretreatment of Corn Stover in Pilot-Scale Reactor" (2003) 105-108 Applied Biochemistry and Biotechnology 69.

Q.A. Nguyen & J.N. Saddler, "An Integrated Model for the Technical and Economic Evaluation of an Enzymatic Biomass Conversion Process" (1991) 35 Bioresource and Technology 275.

Q.A. Nguyen et al., "Dilute Acid Pretreatment of Softwoods", Scientific Note, (1998) 70-72 Applied Biochemistry and Biotechnology 77.

Q.A. Nguyen et al., "Dilute Acid Hydrolysis of Softwoods", Scientific Note, (1999) 77-79 Applied Biochemistry and Biotechnology 133.

Raphael Katzen & Donald F. Othmer, "Wood Hydrolysis. A Continuous Process" (1942) 34 Industrial and Engineering Chemistry 314.

"Transactions of the Institution of Chemical Engineers" (1993) 11 Institution of Chemical Engineers, London, the United Kingdom.

Diane Knappert, Hans Grethlein & Alvin Converse, "Partial Acid Hydrolysis of Cellulosic Materials as a Pretreatment for Enzymatic Hydrolysis" (1980) 22 Biotechnology and Bioengineering 1449.

Sung Bae Kim & Y.Y. Lee, "Diffusion of Sulfuric Acid within Lignocellulosic Biomass Particles and its Impact on Dilute-Acid Pretreatment" (2002) 83 Bioresource Technology 165.

Alan W. Roberts, "Design Considerations and Performance Evaluation of Screw Conveyors", online: The South African Institute of Materials Handling <http://www.saimh.co.za/beltcon/beltcon11/beltcon1114.htm>.

National Renewable Energy Laboratory, "Process Design and Cost Estimate of Critical Equipment in the Biomass to Ethanol Process. Acid Hydrolysis Reactors Batch Systems", Report (Seattle, Washington: Harris Group Inc., 2001).

Osamu Kitani & Carl W.. Hall, eds., "Biomass Handbook" 470-474 (Gordon and Breach Science Publishers: New York).

Buell Classifier Fisher-Klosterman, Leaflet, "Operation Principles and Efficiency".

Process Sensors Corporation, "On-Line Moisture Measurement and Control Manufacturing Industries Worldwide", Product Information, online: Process Sensors Corporation <http://processsensors.com/index.html?gclid=CKT27fXvJOCFREWagodclkUcw>.

Roger M. Rowell, Raymond A. Young, & Judith K. Rowell, eds., Paper and Composites from Agro-Based Resources (Lewis Publishers).

G.H.Emert et al., "Gasohol/Biomass Developments: Economic Update of the Gulf Cellulose Alcohol Process" (Sep. 1980) Chemical Engineering Progress 47.

Ron Kotrba, "The Project of a Lifetime" (Feb. 2006), Ethanol Producer Magazine.

National Renewable Energy Laboratory, "Research Advances: NREL Leads the Way. Cellulosic Ethanol", Brochure, (Mar. 2007), online: National Renewable Energy Laboratory <http://www.nrel.gov/biomass/pdfs/40742.pdf>.

National Renewable Energy Laboratory, Fact Sheet, "Clean Cities: Ethanol Basics" (Oct. 2008), online: U.S. Department of Energy <www.afdc.energy.gov/afdc/pdfs/43835.pdf>.

Brent D. Yacobucci, "Fuel Ethanol: Background and Public Policy Issues", (Mar. 3, 2006), CRS Report for Congress, online: U.S. Department of State, Foreign Press Centre <fpc.state.gov/documents/organization/62837.pdf>.

U.S. Department of Energy, Energy Efficiency & Renewable Energy, Alternative Fuels & Advanced Vehicles Data Center, Article, "Ethanol Market Penetration", online: U.S Department of Energy <http://www.afdc.energy.gov/afdc/ethanol/market.html>.

Kenneth W.Britt, ed., "Handbook of Pulp and Paper Technology", 2nd. ed. (New York: Van Nostrand Reinhold Company).

A. Aden et al., "Lignocellulosic Biomass to Ethanol Process Design and Economics Utilizing Co-Current Dilute Acid Prehydrolysis and Enzymatic Hydrolysis for Corn Stover", (Jun. 2002), Technical Report published by National Renewable Energy Laboratory.

U.S. Department of Energy Office of Science, Genomics Science Program, "Fuel Ethanol Production", online: U.S. Department of Energy Office of Science <http://genomicscience.energy.gov/biofuels/ethanolproduction.shtml>.

Metso Automation, Metso Automation's Newsletter for Neles and Jamesbury products, "Biofuels—a growth market for Metso", (Summer 2008), online: Metso <http://valveproducts.metso.com/metsoautomation/DocDB/catalogs/catalog.taf?pg_parent=397>.

SunOpta Inc., News Release, "SunOpta Announces Sale of Cellulosic Ethanol Facility to China Resources Alcohol Corporation", (Jun. 23, 2006), online: SunOpta Inc. <http://investor.sunopta.com/releasedetail.cfm?ReleaseID=287111>.

Ralph P. Overend, Slideshow, "The Lignocellulosic bottleneck: material properties, architecture and pretreatment".

Robert Wooley et al., "Lignocellulosic Biomass to Ethanol Process Design and Economics Utilizing Co-Current Dilute Acid Prehydrolysis and Enzymatic Hydrolysis Current and Futuristic Scenarios", (Jul. 1999), National Renewable Energy Laborator. Technical Report.

Nathan S. Masier, "Cellulosic Ethanol—Biofuel Beyond Corn" Bio Energy, Purdue University.

U.S Securities and Exchange Commission, "Annual Report Under Section 13 or 15(d) of the Securities Exchange Act of 1934", for Bluefire Ethanol Fuels, Inc. Signed on Feb. 28, 2008.

U.S Securities and Exchange Commission, "Annual Report Under Section 1 or (15)d of the Securities Exchange Act of 1934", for CleanTech Biofuels, Inc. Signed on Mar. 28, 2008.

International Search Report received on the corresponding PCT application No. PCT/CA2010/000088, mailed as a corrected version on Jun. 17, 2010.

International Search Report received in connection to the co-pending international patent application No. PCT/CA2010/000088, mailed on May 14, 2010.

International Search Report received in connection to the co-pending International patent application No. PCT/CA2010/000087, mailed on May 4, 2010.

International Preliminary Report of Patentability received in the corresponding International Application No. PCT/CA2009/001034, issued on Jan. 25, 2011.

International Search Report received on the corresponding International Application No. PCT/CA2009/001034, mailed on Oct. 20, 2009.

Abengoa Bioenergy New Technologies Inc. f/k/a Abengoa Bioenergy R&D, Inc. v. Mascoma Corporation; Notice of Arbitration and Statement of Claim, submitted to American Arbitration Association Commercial Arbitration Tribunal on Nov. 2, 2011.

Ohgren, K., et al., "High Temperature Enzymatic Prehydrolysis Prior to Simultaneous Saccharification and Fermentation of Steam Pretreated Corn Stover for Ethanol Production," 2007, Enzyme Microb Technol, 40/4:607-613.

(56) References Cited

OTHER PUBLICATIONS

Pan, X., et al., "Bioconversion of Hybrid Poplar to Ethanol and Co-Products Using an Organosolv Fractionation Process: Optimization of Process Yields," 2006, Biotech and Bioeng, 94/5:851-861.
Propax Yeast Propagation Technology, Product Brochure, Meura S.A., Edited 2009, 2 pages.
Ramsay, J.A., et al., "Biological Conversion of Hemicellulose to Propionic Acid," 1998, Enzyme Microb Technol, 22:292-295.
Schell, D.J., et al., "A Bioethanol Process Development Unit: Initial Operating Experiences and Results with a Corn Fiber Feedstock," 2004, Bioresource Technology, 91:179-188.
Sharma-Shivappa, R.R., et al, "Conversion of Cotton Wastes to Bioenergy and Value-Added Products," 2008, Transactions of the ASABE, 51/6:2239-2246.
Silwet L-77 Surfactant, Specimen Label, Helena Chemical Company, Copyright 2006, 2 pages.
Sluiter, A., et al., "Determination of Ash in Biomass, Laboratory Analytical Procedure (LAP)," NREL Technical Report, NREL/TP-510-42622, Jan. 2008, 8 pages.
Sluiter, A., et al., "Determination of Extractives in Biomass, Laboratory Analytical Procedure (LAP)," NREL Technical Report, NREL/TP-510-42619, Jan. 2008, 12 pages.
Sluiter, A., et al., "Determination of Structural Carbohydrates and Lignin in Biomass, Laboratory Analytical Procedure (LAP)," NREL Technical Report, NREL/TP-510-42618, Apr. 2008, 16 pages.
Sluiter, A., et al., "Determination of Sugars, Byproducts, and Degradation Products in Liquid Fraction Process Samples, Laboratory Analytical Procedure (LAP)," NREL Technical Report, NREL/TP-510-42623, Jan. 2008, 14 pages.
Sluiter, A., et al., "Determination of Total Solids in Biomass and Total Dissolved Solids in Liquid Process Samples, Laboratory Analytical Procedure (LAP)," NREL Technical Report, NREL/TP-510-42621, Mar. 2008, 9 pages.
Sun, L., "Silicon-Based Materials from Rice Husks and Their Applications," 2001, Ind Eng Chem Res, 40/25:5861-5877, Abstract Only, 1 page.
SUPERFRAC High Performance Trays, Product Brochure, Koch-Glitsch, Bulletin KGSF-1, Revised Mar. 2010, 16 pages.
Taherzadeh, M. J. et al., "Pretreatment of Lignocellulosic Wastes to Improve Ethanol and Biogas Production: a Review," 2008, Int. J. Mol. Sci., (9) 1621-1651.
Teleman, et al., "Progress-Curve Analysis Shows that Glucose Inhibits the Cellotriose Hydrosysis Catalysed by Cellobiohydrolase II from Trichoderma Reesi," 1995, European J Biochem, 231:250-258.
The Artisan Dualflo Tray, Product Brochure, Artisan Industries, Inc., Bulletin 9801, Edit Date Apr. 17, 2003, 2 pages.
Thomas, S., et al., "Biofuels Program C-Milestone Completion Report," FY02, DOE Biofuels Program, Report #373, 2002, 51 pages.
Thomas, S.R., "Corn Stover Feedstock Variability," 2005, Feedstock Area Stage Gate Review Meeting, 34 pages.
Thompson, D.N., et al., "Post-Harvest Processing Methods for Reduction of Silica and Alkali Metals in Wheat Straw," 2002, 24th Symposium on Biotechnology for Fuels and Chemicals, Poster #1-30, 21 pages.
Viamajala, S., et al., "Catalyst Transport in Corn Stover Internodes," 2005, Appl Biochem and Biotech, 129-132:509-527.
Weiss, N.D., et al., "Catalyst Impregnation for High Solids Biomass Pretreatment," 2008, AIChE Annual Meeting, 24 pages.
Yang, B., et al., "Chapter 6. Unconventional Relationships for Hemicellulose Hydrolysis and Subsequent Cellulose Digestion," 2004, Lignocellulose Biodegradation, ACS Symposium Series 889, American Chemical Society, pp. 100-125.
Zimbardi, F., et al., "Acid Impregnation and Steam Explosion of Corn Stover in Batch Processes," 2007, Ind Crops and Products, 26:195-206.
"Biofuels Pilot Plant Under Way," Newsbriefs, Chemical Week, Oct. 13/20, 2008, p. 4.
"Easy Steps for Optimal Yeast Rehydration," Laboratory Protocol, Scott Laboratories, Petaluma CA, 1 page.
"Enzyme Sugar-Ethanol Platform Project," NREL, U.S. Dept. of Energy by Midwest Research Institute, Battelle, Bechtel, 47 pages.
"Ethanol Annual Report FY 1990", SERI, TP-231/3996, Prepared for the U.S. DOE, Jan. 1991, Contract No. DE-AC02-83CH10093, Texeira, R.H. and Goodman, B.J., editors, 344 pages.
"Lessons Learned from Existing Biomass Power Plants," Feb. 2000, NREL/SR-570-26946, G. Wiltsee, Appel Consultants, Inc., Valencia, CA, 149 pages.
"Process Design and Cost Estimate of Critical Equipment in the Biomass to Ethanol Process," Subcontract ACO-9-29067-01, Acid Hydrolysis Reactors Batch System, Report 99-10600/18, NREL, (Prepared by Harris Group Inc., Seattle, Washington, 2001), 36 pages.
"Types of Lignin and Their Properties," 2001, Information Service from the Lignin Institute, 9/1:4 pages, www.lignin.org/01augdialogue.html.
Abstract of Chinese Patent Application CN 101310879 A, 2008, Institute of Process Engineering, Chinese Academy of Sciences.
Activator 90, Product Brochure, 2009, Loveland Products Inc., No. 6566_May 2009, 1 page.
Al-Halaly, A.S.M., "A Study of Some Anatomical Chemical Properties and Specific Gravity of Casuarina Equisetifolia Forst. Wood Grown in Iraq," 1985, AGRIS Record No. IQ8500239, Abstract, 1 page.
Amistco Tower Trays, Product Brochure, Amistco Separation Products, Inc., 8 pages.
Antongiovanni, M., et al., "Variability in Chemical Composition of Straws," 1991, CIHEAM—Options Mediterraneennes, Serie Seminaires, 16:49-53.
Awafo, V.A., et al., "Evaluation of Combination Treatments of Sodium Hydroxide and Steam Explosion for the Production of Cellulase-Systems by Two T. reesei Mutants Under Solid-State Fermentation Conditions," 2000, Bioresource Tech, 73:235-245.
Azadbakht, M., et al.," Preparation of Lignin From Wood Dust as Vanillin Source and Comparison of Different Extraction Methods," Oct. 2004, Int J of Biol and Biotech, 1/4:535-537, Abstract Only, 1 page.
Bakker, R. R., et al., "Biofuel Production from Acid-Impregnated Willow and Switchgrass," 2nd World Conference on Biomass for Energy, Industry and Climate Protection, May 10-14, 2004, Rome, Italy, pp. 1467-1470.
Bigelow, M., et al., "Cellulase Production on Bagasse Pretreated with Hot Water," 2002, App Biochem and Biotech, 98-100:921-934.
Coons, R., "DSM Launches Cellulosic Biofuel Project," Oct. 27, 2008, Chemical Week, 170/33:9.
Coons, R., "Novozymes Ramps Up Focus on Second-Generation Biofuels," Oct. 27, 2008, Chemical Week, 170/33:30.
Cunningham, R.L., et al., "Improved Hemicellulose Recovery From Wheat Straw," 1985, Biotech and Bioeng Symp No. 15, Seventh Symposium on Biotechnology for Fuels and Chemicals, pp. 17-26.
Dasari, R.K., et al., "The Effect of Particle Size on Hydrolysis Reaction Rates and Rheological Properties in Cellulosic Slurries," 2007, Appl Biochem and Biotech, Session 2, 137-140/1-2, 289-299, Abstract Only.
De Castro, F.B., "The Use of Steam Treatment to Upgrade Lignocellulosic Materials for Animal Feed," 1994, Thesis, University of Aberdeen, 214 pages.
Dowe, N., et al., "SSF Experimental Protocols-Lignocellulosic Biomass Hydrolysis and Fermentation, Laboratory Analytical Procedure (LAP)," Jan. 2008, NREL Technical Report, NREL/TP-510-42630, 19 pages.
Esteghlalian, A., et al., "Modeling and Optimization of the Dilute-Sulfuric-Acid Pretreatment of Corn Stover, Poplar and Switchgrass," 1997, Bioresource Technology, 59:129-136.
Fan, L.T., et al., "Evaluation of Pretreatments for Enzymatic Conversion of Agricultural Residues," 1981, Biotechnology & Bioengineering Symposium, 11:29-45 (Proceedings of the Third Symposium on Biotechnology in Energy Production and Conservation, Gatlinburg, TN, May 12-15, 1981.
Flexitray Valve Trays, Product Brochure, Koch-Glitsch, Bulletin FTCVT-01, Revised Mar. 2010, 12 pages.
Flint, S.I., et al., "Recovery of Lignin During Nonstarch Polysaccharide Analysis," 1992, Cereal Chem, 69/4:444-447.

(56) References Cited

OTHER PUBLICATIONS

Foody, P., "Optimization of Steam Explosion Pretreatment," 1980, Final Report to DOE, Report No. DOE/ET23050-1, Contract No. ACO2-79ET23050, Bibliographic Citation, 1 page.
Fuel Ethanol Application Sheet, "CELLIC Ctec and Htec2—Enzymes for Hydrolysis of Lignocellulosic Materials," Novozymes A/S, Luna No. 2010-01668-01, 9 pages.
GEA Wiegand, GmbH, Process Engineering Division, "Bioethanol Technology", Ettlingen, Germany, Company Brochure, 16 pages.
GEA Wiegand, GmbH, Process Engineering Division, "Distillation Technology", Ettlingen, Germany, Company Brochure, 16 pages.
Ghose, T.K., "Measurement of Cellulase Activities," 1987, Pure and Appl. Chem., 59/2:257-268.
Grethlein, H.E., "Chemical Breakdown of Cellulosic Materials," 1978, J. Appl. Chem. Biotechnol. 28:296-308.
Grethlein, H.E., et al., "Common Aspects of Acid Prehydrolysis and Steam Explosion for Pretreating Wood," 1991, Bioresource Technology, 36:77-82.
Grohmann, K, et al., "Optimization of Dilute Acid Pretreatment of Biomass," Proceedings of the Seventh Symposium on Biotechnology for Fuels and Chemicals, May 14-17, 1986, 24 pages.
Hames, B., et al., "Determination of Protein Content in Biomass, Laboratory Analytical Procedure (LAP)," May 2008, NREL Technical Report, NREL/TP-510-42625, 8 pages.
Hames, B., et al., "Preparation of Samples for Compositional Analysis, Laboratory Analytical Procedure (LAP)," Aug. 2008, NREL Technical Report, NREL/TP-510-42620, 12 pages.
International Search Report and the Written Opinion issued in connection with PCT Application No. PCT/CA2009/001032, mailed on Oct. 27, 2009, 11 pages.
International Search Report and the Written Opinion issued in connection with PCT Application No. PCT/CA2009/001035, dated Nov. 5, 2009, 7 pages.
International Search Report and the Written Opinion issued in connection with international application No. PCT/CA2009/001033, mailed on Oct. 30, 2009.
International Search Report and the Written Opinion issued in connection with PCT Application No. PCT/US2010/46561, dated Dec. 20, 2010, 16 pages.
International Search Report and the Written Opinion issued in PCT Application No. PCT/US20121022552, dated May 15, 2012, 18 pages.
Written Opinion of the International Searching Authority, dated Oct. 8, 2010, corresponding to International application No. PCT/CA2010/001091.
PCT International Search Report, dated Oct. 8, 2012, corresponding to International application No. PCT/CA2010/001091.
Juhasz, T., et al., "Characterization of Cellulases and Hemicellulases Produced by Trichoderma reesei on Various Carbon Sources," 2005, Process Biochem, 40:3519-3525.
Keller, F.A., et al., "Yeast Adaptation on Softwood Prehydrolysate," 1998, Appl Biochem and Biotech, 70-72:137-148.
Kolar, L, et al., "Agrochemical Value of Organic Matter of Fermenter Wastes in Biogas Production," 2008, Plant Soil Environ, 54/8:321-328.
Kumar, R., et al., "The Impact of Dilute Sulfuric Acid on the Selectivity of Xylooligomer Depolymerization to Monomers," 2008, Carbohydrate Res, 343:290-300.
Linde, M., et al., "Steam Pretreatment of Acid-Sprayed and Acid-Soaked Barley Straw for Production of Ethanol," 2006, Appl Biochem and Biotech, 129-132:546-562.
Liu, H., et al., "Lignin-Metal Complexation to Eliminate Nonproductive Enzyme Adsorption by Lignin in Unwashed Lignocellulosic Substrates," 2010, 32nd Symposium on Biotechnology for Fuels and Chemicals, 28 pages.
Office action issued in Canadian Application No. 2,638,152, dated Feb. 8, 2011, 4 pages.

\* cited by examiner

METHOD AND APPARATUS FOR CONVEYING A CELLULOSIC FEEDSTOCK

FIELD

The invention relates to a method and apparatus for preparing a cellulosic feedstock for the subsequent production of a fermentable sugar stream from the cellulose and hemicellulose in the cellulosic feedstock wherein the fermentable sugar stream may be used for subsequent ethanol production. More specifically, the invention relates to a holding tank, and a method of utilizing the holding tank to prepare a cellulosic feedstock that may result in a product stream from autohydrolysis or hydrolysis having an improved yield.

BACKGROUND

Several processes for the production of ethanol are known. Generally, the production of fuel ethanol involves the fermentation of sugars with yeast. Typically, the sugars are derived from grains, such as corn and wheat. The starches in the grains are subjected to enzymatic hydrolysis in order to produce the sugars, which are then subjected to fermentation to produce ethanol.

Plant materials are a significant source of fermentable sugars, such as glucose that can be transformed into biofuels. However, the sugars in plant materials are contained in long polymeric chains of cellulose and hemicellulose. Utilizing current fermentation processes, it is necessary to break down these polymeric chains into monomeric sugars, prior to the fermenting step.

Recently, processes have been developed for utilizing cellulosic feedstock, such as corncobs, straw, and sawdust, to produce sugars for ethanol fermentation. Such processes typically comprise pre-treating the feedstock to increase the accessibility of the cellulose to hydrolysis enzymes, and subjecting the cellulose to cellulase enzyme systems to convert the cellulose into glucose.

Methods of converting plant biomass into fermentable sugars are known in the art and in general comprise two main steps: a pre-treatment step to activate the plant structure, and an enzymatic or chemical hydrolysis step to convert the polymeric chains of cellulose and hemicellulose into monomeric sugars. Several approaches have been used for the pre-treatment step, e.g., autohydrolysis, acid hydrolysis, ammonia activation, kraft pulping, organic solvent pulping, hot water pre-treatment, ammonia percolation, lime pre-treatment, caustic soda pulping, or alkali peroxide pre-treatment. Early pre-treatment steps included grinding or milling the feedstock into a powder, which was then mixed with water to form a slurry.

More recently, solvent based pre-treatments, alkali pre-treatments, and acidic pre-treatments have also been described. PCT publication WO/2007/009463 to Holm Christensen describes an alternate pre-treatment, which does not involve the addition of acids, bases, or other chemicals. This pre-treatment process involves soaking the cellulosic material in water, conveying the cellulosic material through a heated and pressurized reactor, and pressing the cellulosic material to produce a fiber fraction and a liquid fraction. After pressing the cellulosic material, the cellulosic material is exposed to hydrolysis enzymes.

Each pre-treatment technology has a different mechanism of action on the plant structure, inducing either physical and/or chemical modifications. However, the main objective of the pre-treatment is to provide accessibility of the plant material to the enzymes.

SUMMARY

The commercial viability of a hydrolysis process is dependent on the character of the feedstock provided to the hydrolysis unit. Typically, this requires that a feedstock is activated such that a significant portion (e.g., greater than 75%) of the cellulose and hemicellulose of the feedstock is accessible to hydrolysis enzymes. If such an activated feedstock is provided to an enzymatic hydrolysis unit, then at least 60%, preferably more than 75% and more preferably over 90% of the cellulose and hemicelluloses may be converted to monomeric sugars. This sugar rich process stream may subsequently be subjected to fermentation to produce an alcohol stream. The alcohol stream from the fermentation stage (i.e., the raw alcohol stream) may have an ethanol content of about 3-22% v/v, preferably about 5-15% and more preferably more about 8-12%.

An activated feedstock for enzymatic hydrolysis is preferably prepared by auto hydrolysis, which is preferably conducted in a steam explosion reactor also known as a hydrolyzer, (also known as a digester). Auto hydrolysis is a process of breaking down hemicellulose and cellulose by exposure to high temperatures, steam and pressure, sometimes in the presence of an added chemical agent, such as an organic or inorganic acid, e.g., sulphuric acid. When performed in the presence of an added acid, the reaction is known as acid hydrolysis.

During auto hydrolysis, the degree of polymerization of cellulose and hemicellulose may be reduced from about 10,000 to about 1,500-1,000. This process is preferably carried out above the glass transition temperature of lignin (120-160° C.). Depending upon the severity of the reaction, degradation products may be produced, such as furfural, hydroxyl-methylfurfural, formic acid, levulinic acid and other organic compounds.

During a steam explosion treatment (more commonly called autohydrolysis if no externally added catalyst, a cellulosic feedstock is subjected to elevated heat (e.g 180° C. to 220° C.) and pressure (e.g., 131 psig to 322 psig) optionally in the presence of suitable chemicals (e.g., organic and/or inorganic acids, ammonia, caustic soda, sulfur dioxide, solvents etc.) in a pressurized vessel. Preferably, external chemical addition is not utilized, in which case, the only catalyst that may be present may be acetic acid that is generated in situ. The treated cellulosic feedstock is then released from the pressurized vessel such that the pressure is rapidly reduced (e.g., 1 second or less). The biomass may exit the hydrolyzer into a reduced pressure, preferably atmospheric pressure and, more preferably into a vacuum. The rapid decrease in pressure results in the biomass separating into individual fibers or bundles of fibers. This step opens the fiber structure and increases the surface area. The lignin remains in the fiber along with cellulose and residual hemicellulose. Accordingly, the explosive release of pressure, combined with the high temperature and pressure treatment results in the physico-chemical modification of the cellulosic feedstock that is then suitable for feeding to an enzymatic hydrolysis unit.

In order for the steam explosion process to be able to produce an activated feedstock that is capable of producing such a sugar rich process stream, the temperature and moisture level of the cellulosic feedstock that is fed to a steam explosion reactor preferably is relatively uniform and preferably has a temperature from about 50 to about 70° C., and more preferably 50-65° C. and a moisture content from about 30 to about 60 wt % (preferably 45 to about 55 wt %). Moisture content is the quantity of water contained in a material, and on a weight basis, is the weight of water in the material divided by the mass of the material.

Without being limited by theory, it is believed that an unexpected increase in the conversion of the feedstock to fermentable sugars may be achieved if the moisture content of the feedstock fed to the steam explosion reactor is lower, provided that sufficient water is present for hydrolyzing and/or activating the feedstock. If the feedstock is too dry, then there may be insufficient water molecules present in the fiber and hence not all of the feedstock will be activated and/or hydrolyzed (i.e., the hydrolysis reaction/activation will not occur at all possible sites). Accordingly, it might be presumed that a substantial excess of water should be used to ensure water molecules are available at each hydrolysis/activation site. Surprisingly, it has been determined that if the cellulosic feedstock that is fed to a steam explosion reactor has an excess of moisture then a smaller percentage of the available sites of the feedstock are activated/hydrolyzed than would be expected. It is believed that this is due to the high moisture content acting as a barrier to heat transfer through the fiber structure. The external fiber reaches the process temperature far in advance to the internal fiber, hence resulting in very uneven heat transfer and the resulting uneven autohydrolysis reaction. Further, during the autohydrolysis process additional water may be provided to the process by way of direct injected steam in order to raise the fiber temperature from the inlet temperature to the outlet temperature of the reactor. If the inlet moisture content of the fiber is at saturation, then the additional water will be free water in the autohydrolysis reactor resulting in washing of the soluble hemicellulose from the fiber and causing subsequent accumulation of hemicellulose within the reactor. Over time, the accumulated hemicellulose will tend to break down to inhibitor compounds and deposit degraded sugars on the internal components of the reactor. These deposits will become an obstruction to the flow of the biomass.

It has also been determined that if the cellulosic feedstock that is fed to a hydrolyzer has a temperature that is too high, then some percentage of the hemicellulose sugars will be degraded to inhibitory compounds prior to starting the autohydrolysis reaction and further amounts during the autohydrolysis reaction itself. Conversely, if the fiber is too cold entering the hydrolyzer, the first one third to one half of the reactor vessel may act as a preheating device rather than as a hydrolyzer, resulting in incomplete autohydrolysis. Accordingly, it is preferred to have very consistent fiber temperature year round as well as from night to day time operation, for the fiber that is fed to the hydrolyzer.

Alternately, and in addition, it is preferred that the fiber in the feedstock fed to the autohydrolysis unit have a relatively uniform temperature profile. For example, it is preferred that the core of the blocks of material have a temperature that is within 80%, more preferably 90%, most preferably 95% of the temperature of the exterior surface of the material. Accordingly, for example, if the temperature of the exterior surface of the material is from 50 to 70° C., then the temperature of the core of the material is preferably from 45 to 63° C.

It has also been determined that the fiber requires time for the moisture that is added to become equilibrated throughout the entire fiber particle. It has been determined that under laboratory conditions, it may take from 5 to 9 minutes to equilibrate the moisture content of the fiber. Under industrial conditions it will be longer. Preferably, the autohydrolysis reaction time in the vessel is typically about 5 to 6 minutes or less. It is preferred that the fiber in the feedstock fed to the autohydrolysis unit have a relatively uniform moisture profile. For example, it is preferred that the core of the blocks of material have a moisture content that is within 80%, more preferably 90%, most preferably 95% of the moisture content of the exterior surface of the material. Accordingly, for example, if the moisture content of the exterior surface of the material is from 45 to 55 wt %, then the moisture content of the core of the material is preferably from 40.5 to 49.5 wt %.

A feedstock having a moisture content from about 30 to about 60 wt % may be prepared by obtaining relatively dry plant material which is broken down into small chips, e.g., from about 0.05 to about 2 inches, and then combining the chips with water (e.g., steam and/or a fine mist spray, or droplets of water of between 600 μ and 6000 μ in diameter). This material may then be transported to a hydrolysis or autohydrolysis reactor, and preferably is subjected to autohydrolysis and then subsequently enzymatic hydrolysis. This material is difficult to transport as the material is essentially a solid (having insufficient water to form even a slurry). Accordingly, the material has a tendency to interlock and may result in process vessels or flow passages between equipment becoming blocked. Also, since this material is essentially discrete blocks of material (e.g., wood chips), the gaps between the blocks are filled with air. Accordingly, the mass and heat transfer characteristics of this material result in it being difficult to obtain a relatively uniform distribution of heat and moisture in the material. This lack of uniformity can result in decreased yield and/or contamination during downstream autohydrolysis or enzymatic hydrolysis.

Embodiments of the present invention provide a method and apparatus for conveying a cellulosic feedstock. The method and apparatus relate to a holding tank that can be positioned downstream from a cellulosic feedstock pre-treatment process, preferably an impregnation process wherein moisture is added to the feedstock but the feedstock is not converted to a slurry, that can be utilized to further prepare the cellulosic feedstock for subsequent production of a sugar stream, which is preferably fermented to produce alcohol. Preferably, the feedstock is subsequently subjected to a hydrolysis process. The hydrolysis process may be autohydrolysis and, more preferably, comprises autohydrolysis followed by enzymatic hydrolysis.

In one broad aspect, a method for preparing a cellulosic feedstock for subsequent ethanol production is provided. The method comprises obtaining a cellulosic feedstock having a moisture content of 30% to 60%; passing the cellulosic feedstock through a heated holding tank; withdrawing the cellulosic feedstock from the holding tank; and, subsequently subjecting the cellulosic feedstock to hydrolysis.

In some embodiments, the moisture content of the cellulosic feedstock is between 45% and 55%.

In some embodiments, the step of passing the cellulosic feedstock through a heated holding tank comprises passing the cellulosic feedstock downwardly through the heated holding tank. In further embodiments, the cellulosic feedstock is passed downwardly through the heated holding tank under the force of gravity.

In some embodiments, the cellulosic feedstock has a residence time of up to 60 minutes in the heated holding tank. In some further embodiments, the cellulosic feedstock has a residence time of between 5 minutes and 45 minutes in the heated holding tank. In yet further embodiments, the cellulosic feedstock has a residence time of between 10 minutes and 30 minutes in the heated holding tank.

In some embodiments, the heated holding tank is heated by passing a heated fluid through a heating jacket provided on at least a portion of the heated holding tank.

In some embodiments, the cellulosic feedstock enters the heated holding tank at a temperature of between 50° C. and 70° C. In some further embodiments, the cellulosic feedstock enters the heated holding tank at a temperature between 50° C. and 65° C.

In some embodiments, the method further comprises maintaining the cellulosic feedstock at a temperature of between 50° C. and 70° C. while in the heated holding tank. In alternate embodiments, the cellulosic feedstock enters the heated holding tank at a first temperature, and exits the heated holding tank at a second temperature higher than the first temperature. In some such embodiments, the first temperature is below 50° C., and the second temperature is between 50° C. and 70° C.

In some embodiments, the heated holding tank has a lower open end, and the step of withdrawing the cellulosic feedstock from the holding tank comprises withdrawing cellulosic feedstock from essentially the entirety of the lower open end.

In some embodiments, the method further comprises monitoring a temperature of the cellulosic material in the heated holding tank. In some further embodiments, the method comprises adjusting an amount of heat applied to the heated holding tank based on the temperature of the cellulosic material in the holding tank.

In some embodiments, the method comprises obtaining the cellulosic feedstock from a water impregnation reactor.

In accordance with another broad aspect, a holding tank apparatus for preparing a cellulosic feedstock is provided. The holding tank apparatus comprises at least one sidewall defining a passage having an upper portion and a lower portion. At least one inlet is provided adjacent the upper portion, wherein, in use, the inlet is in fluid communication with a water impregnation reactor provided upstream from the holding tank. At least one outlet is provided adjacent the lower portion, wherein, in use, the inlet is in fluid communication with hydrolysis reactor positioned downstream from the holding tank. At least one conveyor is positioned adjacent to at least one outlet. A heating jacket provided on at least a portion of the apparatus.

In some embodiments, the heating jacket is provided on the sidewalls of the holding tank.

In some embodiments, the at least one conveyor conveys the cellulosic feedstock laterally across the outlet. Preferably, the outlet extends across the lower portion of the passage. In some further embodiments, the holding tank has a longitudinal axis, and each of the at least one conveyors comprises a screw conveyor extending transversely to the longitudinal axis and provided in a housing positioned adjacent the outlet, and the housing comprises a second heating jacket.

In some embodiments, the holding tank is operable to provide a residence time of up to 60 minutes. In some further embodiments, the holding tank is operable to provide a residence time of between 5 minutes and 45 minutes.

In some embodiments, the holding tank has a longitudinal axis and at least one of the at least one sidewalls diverges from the longitudinal axis from the upper portion to the lower portion.

An advantage of this process is that the temperature of the feedstock is maintained at a suitable temperature for feeding to a steam explosion reactor while the temperature may be kept sufficiently low to prevent charring of the fibers. Charring of the fibers results in degradation of the sugars in the cellulose and hemicellulose. This degradation reduces the percentage of sugars that may be liberated for fermentation, thereby decreasing the possible yield of the process. Further, the degradation may produce by-products that are undesirable in downstream process streams. Further additional time may be provided to enhance the uniformity of the water distribution in the fiber chips such that water is available at essentially all sites for hydrolysis.

BRIEF DESCRIPTION OF THE DRAWINGS

These and other advantages of the present invention will be more fully and particularly understood in connection with the following description of the preferred embodiments of the invention in which.

DETAILED DESCRIPTION

Figure 1:
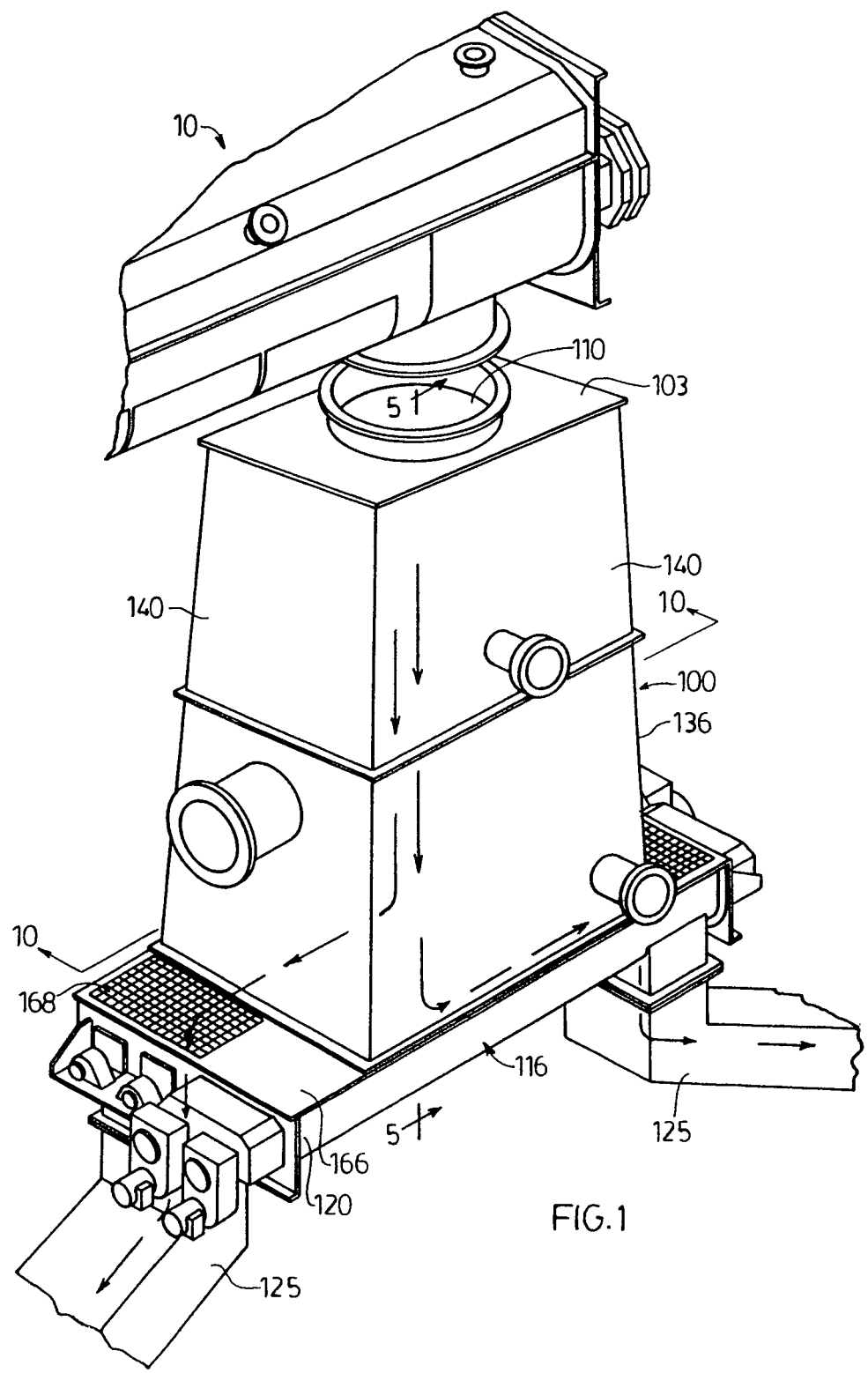
FIG. 1 is a perspective illustration of an embodiment of a holding tank of the present invention, showing an impregnation chamber positioned upstream from the holding tank.

Embodiments of the present invention provide a method and apparatus for treating a cellulosic feedstock for subsequent ethanol production. The method and apparatus of the preferred embodiment serve to heat or maintain the temperature of the cellulosic feedstock to obtain a relatively uniform temperature and moisture level of the feedstock, while reducing, and preferably essentially preventing, the charring or other degradation of the cellulose and hemicellulose during this stage. Accordingly, the method and apparatus provide a cellulosic feedstock which is suitable for the production of a fermentation precursor stream. The cellulosic feedstock may be subsequently treated to liberate sugars in the cellulose and hemicellulose and produce a sugar stream that may then be subjected to fermentation to obtain a high yield alcohol stream. An embodiment of an apparatus of the present invention is shown in FIGS. 1-10. It will be appreciated that although the method is described with reference to the apparatus and vice versa, the method may be carried out with an alternate apparatus, and the apparatus may be used according to an alternate method. Furthermore, although the method is described as a continuous process, it will be appreciated that the method may be carried out as a semi-continuous or batch process.

The cellulosic feedstock is preferably a lignocellulosic feedstock. A lignocellulosic feedstock is derived from plant materials. As used herein, a "lignocellulosic feedstock" refers to plant fiber containing cellulose, hemicellulose and lignin. In some embodiments, the feedstock may be derived from trees, preferably deciduous trees such as poplar (e.g., wood chips). Alternately or in addition, the feedstock may also be derived from agricultural residues such as, but not limited to corn stover, wheat straw, barley straw, rice straw, switchgrass, sorghum, bagasse, rice hulls and/or corn cobs. Preferably, the lignocellulosic feedstock comprises agricultural residues and wood biomass, more preferably wood biomass and most preferably deciduous. The applicants contemplate other sources of plant materials comprising cellulose, hemicellulose and/or lignin, such as algae, for use in deriving cellulosic feedstocks and any of those may be used.

The lignocellulosic feedstock is preferably cleaned, e.g., to remove ash, silica, metal strapping (e.g., from agricultural products), stones and dirt. The size of the components of the lignocellulosic feedstock may also be reduced. The size of the components of the feedstock may be from about 0.05 to about 2 inches, preferably from about 0.1 to about 1 inch, and more preferably from about 0.125 to about 0.5 inches in length. For example, the cellulosic feedstock may comprise fibers, e.g., chopped straw, of a length of between about 0.16 inches and about 0.28 inches. Any process machinery that is able to crush, grind or otherwise decrease the particle size may be utilized.

The feedstock is preferably treated with water so as to have a moisture content upon entry to holding tank 100 of between about 30 and about 60, preferably between about 45 and about 55 wt %. For example, referring to FIGS. 1 and 2, an embodiment of a holding tank apparatus 100 of the present invention is shown wherein the holding tank 100 is positioned downstream from a water impregnation reactor such as impregnation chamber 10, which is preferably used to pre-treat the feedstock prior to the feedstock entering holding tank 100. Impregnation chamber 10 is preferably configured to pre-treat the cellulosic feedstock, for example by moistening and/or heating the cellulosic feedstock.

Figure 2:
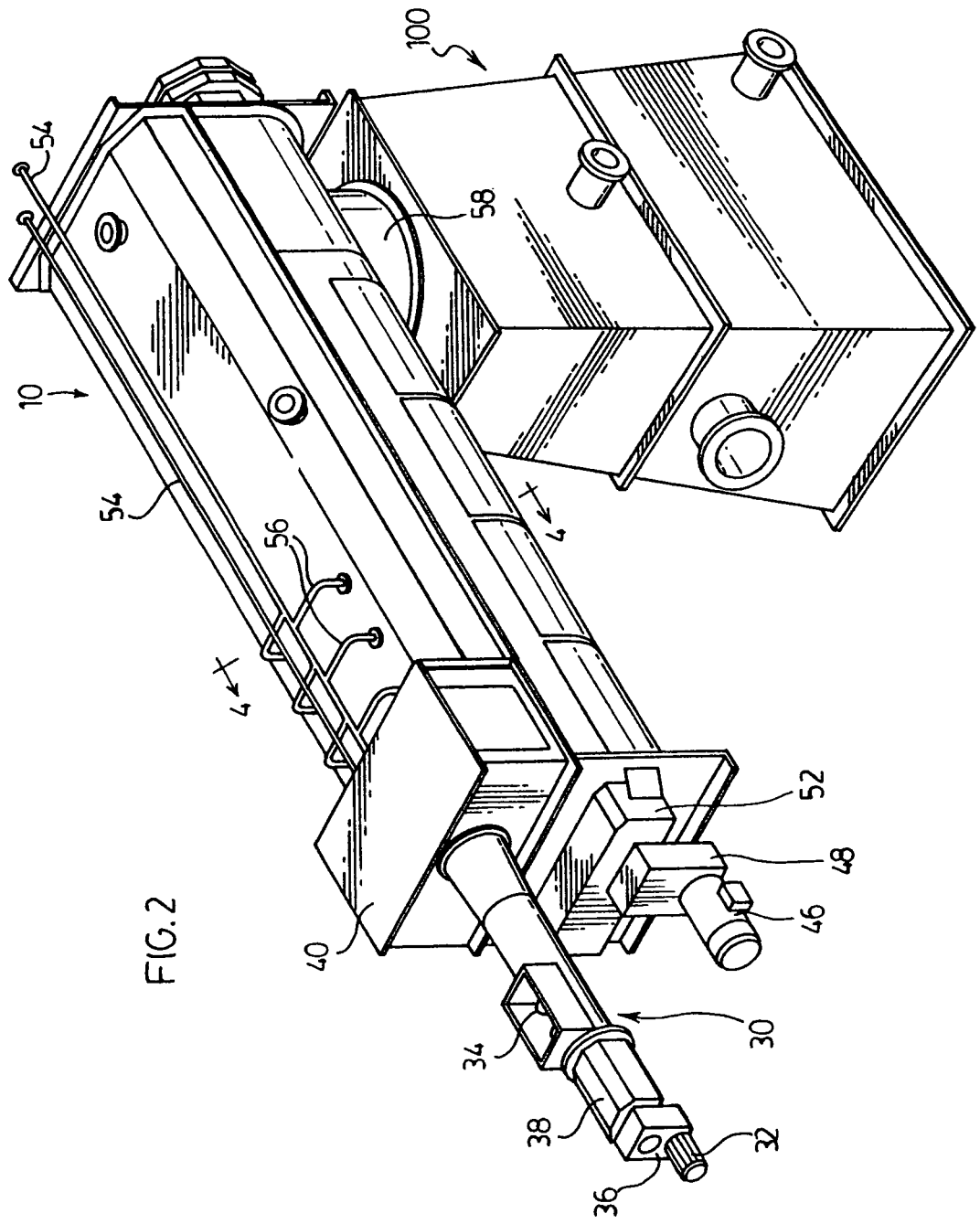
FIG. 2 is a perspective illustration of the impregnation chamber of FIG. 1.
Figure 3:
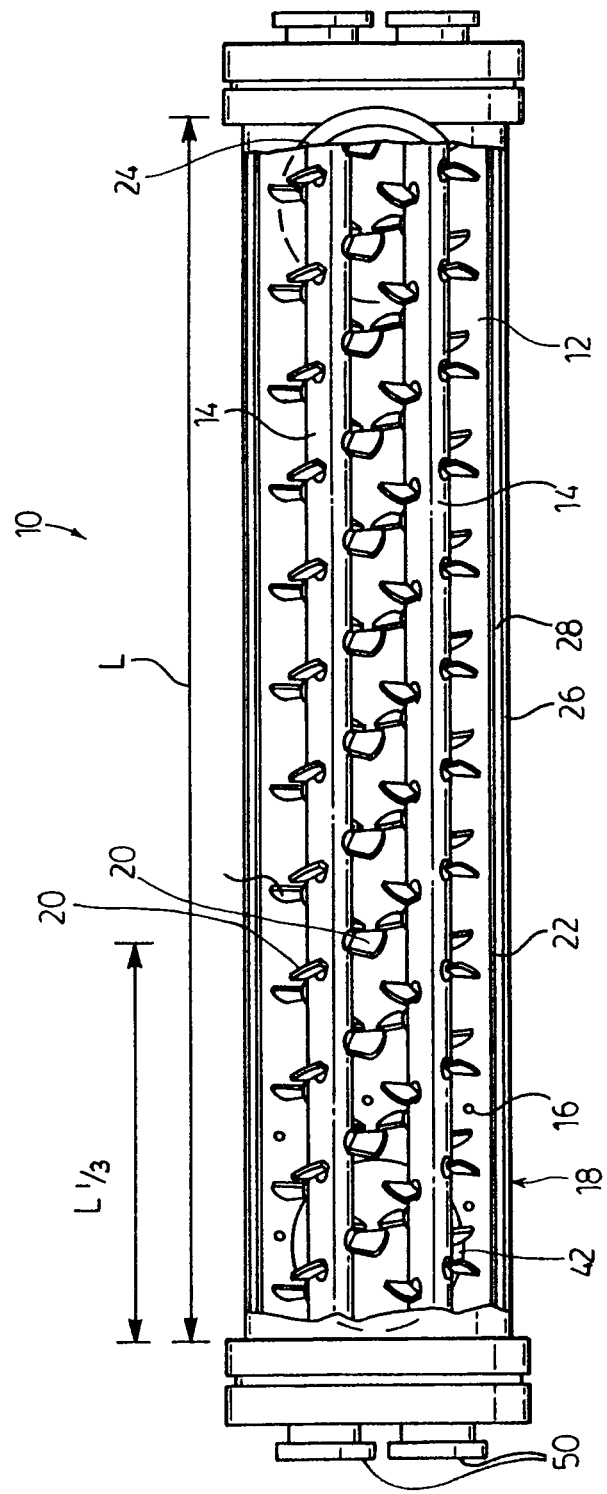
FIG. 3 is a top cutaway view of the impregnation chamber of FIG. 1.
Figure 4:
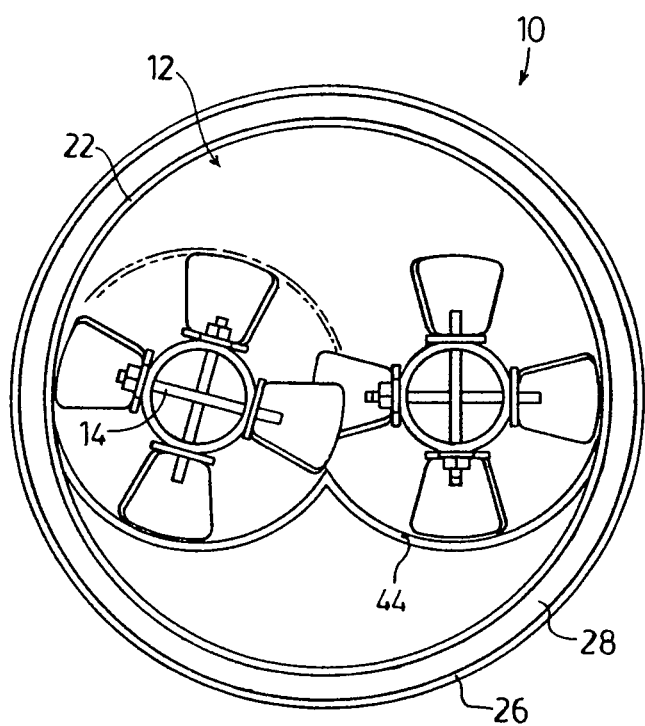
FIG. 4 is a cross section taken along line 4-4 in FIG. 2.

A preferred impregnator 10 is exemplified in FIGS. 2-4. As shown therein, in some embodiments, an impregnator feeder 30, namely a feeder that conveys feedstock into impregnation chamber 12, is preferably positioned upstream of mixing or impregnation chamber 12. Feeder 30 may be of any design. Preferably, feeder 30 is of a design that inhibits, and preferably prevents, the flow of moisture upstream of feeder 30. For example, a rotating valve or the like may be provided to segment such upstream flow. Preferably impregnation feeder is a screw feeder comprising a motor 32 drivingly connected to a screw or auger 34 positioned below an inlet, such as via a transmission or gear reduction assembly provided in housing 36. The shaft on which screw 34 is provided may be rotatably mounted in housing 38 such that auger 34 is a cantilevered plug screw conveyor. Accordingly, feeder 30 produces a plug of material that prevents upstream migration of moisture. The plug may be conveyed into inlet housing 40 that is mounted to impregnation chamber 12. The feedstock may then pass downwardly into impregnation chamber 12.

Impregnator 10 may comprise an inlet 42 positioned below inlet housing 40, one or more conveyance members 14 for urging the cellulosic feedstock along the length of chamber 12, one or more moisture injection ports 16, which may be provided on paddles 20 of conveyance member 14 and/or inner wall 22 of impregnator 10, for injecting moisture into the cellulosic feedstock one or more heating jackets 18 provided outward of inner wall 22 for heating the cellulosic feedstock, and an outlet 24. Heating jacket 18 may comprise an outer wall 26 spaced from inner wall 22 to define a passage 28 through which a heated fluid, e.g. water, may pass.

As exemplified in FIG. 2, one or more conduits 54 may convey water to a plurality of branch conduits 56 extending to different locations on the upper portion of chamber 12. The end of these conduits are in fluid flow communication with the interior of chamber 12, via, e.g., a moisture addition member such as a nozzle or an open ended pipe or the like.

As exemplified, conveyance members 14 are rotatably mounted in chamber 12 and are drivenly connected to a motor 46. As exemplified, motor 46 is drivingly connected to conveyance members 14 via a transmission or gear reduction assembly provided in housing 48. The gear reduction assembly may be drivingly connected to ends 50 of conveyance members 14 that are positioned inside housing 52.

In order to prevent material stagnating in impregnator 10, impregnator 10 may have a bottom wall 44 that has two or more portions each of which has a conveyance member 14 associated therewith. Bottom wall 44 and conveyance member 14 are preferably configured such that bottom wall 44 is swept as conveyance member 14 rotates. For example, as exemplified in FIG. 4, bottom wall 44 may be scallop shaped, e.g., have two inverted arches or troughs. Further details regarding various embodiments of optional impregnation chamber 14 may be found in U.S. Publication No. 20100028089 A1, the disclosure of which is incorporated herein by reference in its entirety. In alternate embodiments, impregnation chamber 10 may pre-treat the cellulosic feedstock in another manner, and the invention is not limited in this regard.

After the cellulosic feedstock is optionally pre-treated in impregnation chamber 10, it is directed to holding tank apparatus 100, e.g., via outlet passage 58 that is downstream from outlet 24 of chamber 12, where it is held or contained for a residence time, such that for example, moisture added in impregnation chamber 10 has sufficient time to penetrate into the feedstock so that the feedstock is ready for downstream processing. Alternately, or in addition, the feedstock may require additional time for all portions of the feedstock to be raised to a predetermined temperature that is suitable for downstream processing. Alternately, the feedstock entering holding tank 100 may be at the predetermined conditions for downstream processing and holding tank is used as a reservoir to hold prepared feedstock such that downstream processes may operate on a continuous basis. From holding tank 100, the cellulosic feedstock may be directed to one or more hydrolysis reactors, preferably one or more autohydrolysis reactors followed by one or more enzymatic hydrolysis reactors (not shown) positioned downstream from the holding tank apparatus 100, such that the cellulose may be hydrolyzed to produce sugars that are suitable for fermentation to ethanol.

Figure 5:
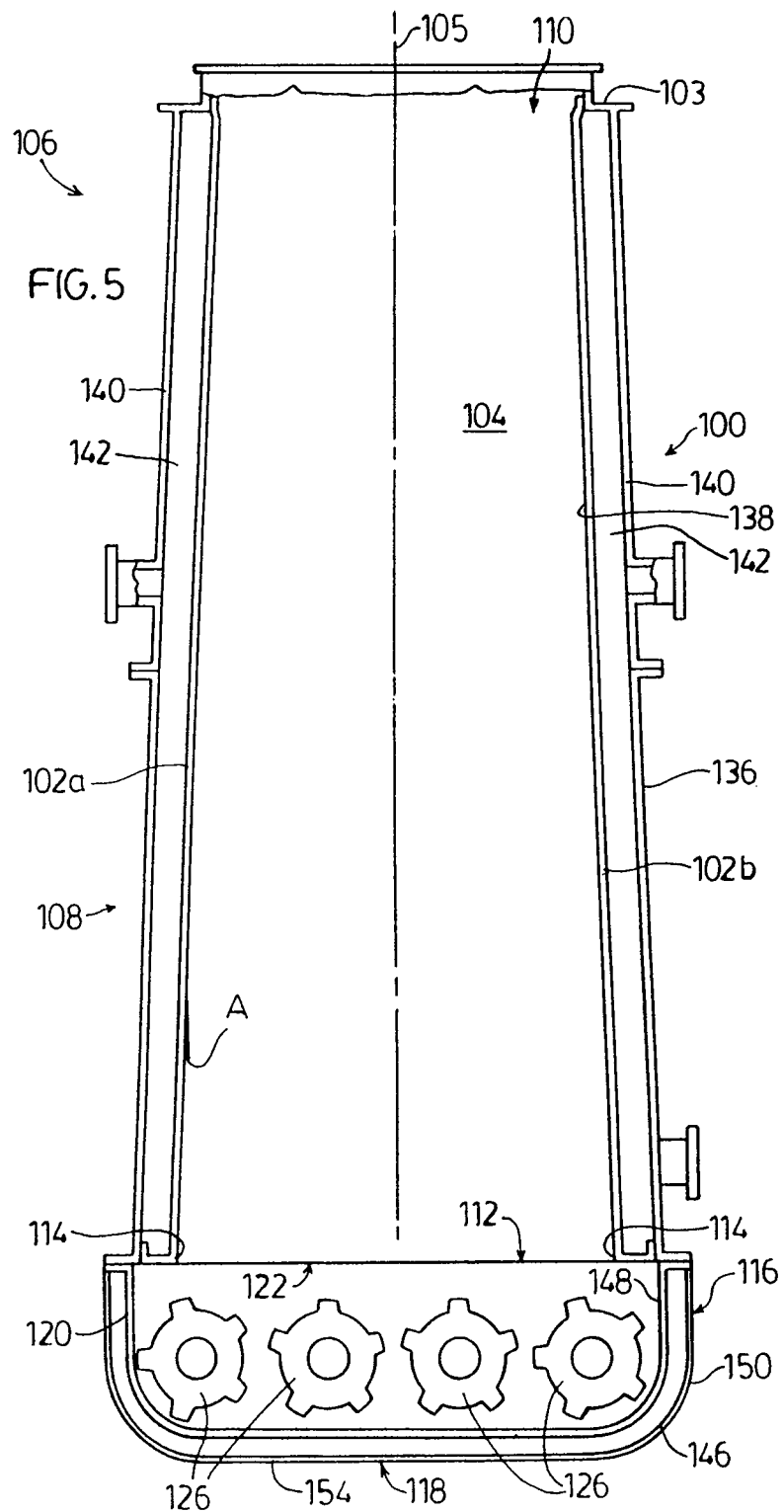
FIG. 5 is a cross section taken along line 5-5 in FIG. 1.

As exemplified in FIGS. 1 and 5, holding tank 100 is preferably oriented such that the passage through holding tank 100 extends generally downwardly and the passage therethrough is configured so as to reduce, and preferably essentially prevent, bridging of feedstock in holding tank 100. Further, the passage from impregnator 10 to holding tank 100 preferably extends generally downwardly. Accordingly, it is preferred that the passage through holding tank 100 extends generally downwardly and that the passage has a greater cross sectional area at the lower end then the upper end. More preferably, the cross sectional area continually increases in the downward direction. This may be achieved by constructing the passage of the holding tank with one or more walls that diverge in the downward direction.

If the feedstock passing downwardly through holding tank 100 interlocks, it may form a blockage by a process known as bridging. The blockage may extend all the way across the passage in holding tank 100 thereby preventing downward movement of feedstock and causing a gap in the supply of feedstock to the downstream process unit. Alternately, it may block only part of the passage. In any event, intervention would then be required to remove the blockage. The interruption of feedstock delivery to the downstream process unit could require part of a plant to be shut down while the blockage is removed thereby reducing throughput and also requiring the plant to be brought back to steady state operating conditions once the blockage is cleared. Accordingly, the holding tank may require monitoring to permit intervention at an early stage should bridging occur. By increasing the cross sectional area in the downstream direction, the tendency of the feedstock to form a blockage of the passage is reduced and may be eliminated.

Figure 10:
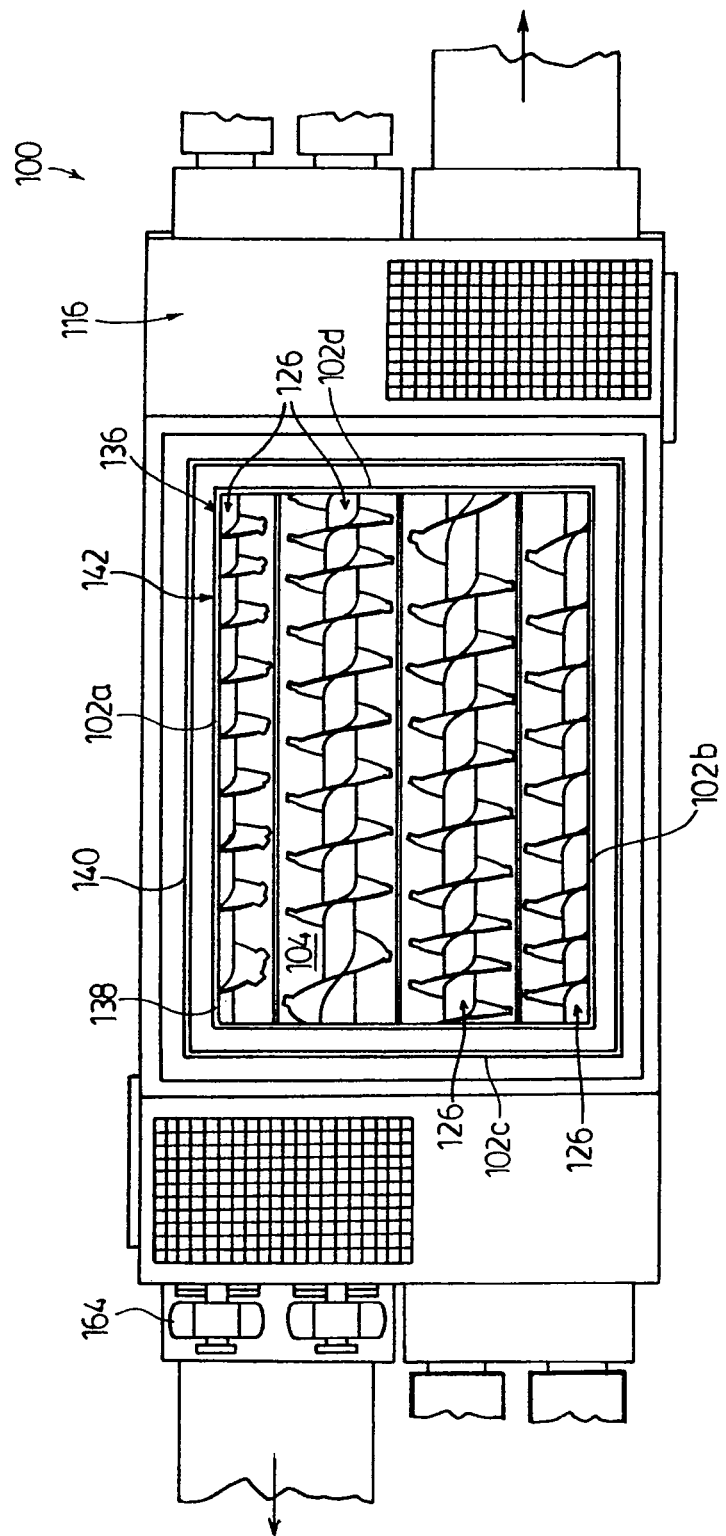

As exemplified in FIGS. 5 and 10, holding tank 100 comprises at least one sidewall 102, which defines a volume or passage 104. In the embodiment shown, holding tank apparatus 100 comprises four sidewalls, namely front wall 102a, and a spaced apart opposed rear wall 102b, and a side wall 102c and a spaced apart opposed side wall 102d, and further comprises a top wall 103. Accordingly, passage 104, which is defined by sidewalls 102a, 102b, 102c and 102d is rectangular in transverse section. In other embodiments, holding tank apparatus 100 may comprise, for example, a single rounded sidewall so as to have a transverse section that is circular, elliptical or the like. It will be appreciated that any other transverse section may be utilized.

Passage 104 is preferably longitudinally extending, for example along axis 105, and comprises an upper portion 106, and a lower portion 108. Passage 104 preferably extends vertically. However passage may extend generally vertically (i.e., at an angle to the vertical such that feedstock will flow downwardly therethrough under the force of gravity). In some embodiments, volume 104 may have a length along axis 105 of between about 5 ft and about 20 ft.

An inlet 110 is provided adjacent upper portion 106, and an outlet 112 is provided adjacent lower portion 108, at an elevation below the inlet 110. In the embodiment shown, inlet 110 is defined by an opening in top wall 103, and outlet 112 is defined by the lower ends 114 of sidewalls 102. It will be appreciated that inlet 110 may comprise the entirety of the top end of holding tank 100 and accordingly, a top wall 103 may not be required. It will be appreciated that in the preferred embodiment, no lower surface is provided for passage 104 and that the lower end of passage 104 is open. Accordingly, feedstock may flow downwardly through passage 104 unimpeded until it encounters feedstock stored in holding tank 100 or until it encounters housing 116. As exemplified, inlet 110 is in fluid communication with and receives cellulosic feedstock from outlet 24 of impregnator 10 (e.g., it is downstream of outlet conduit 58), and outlet 112 is preferably in fluid communication with and directs cellulosic feedstock to one or more autohydrolysis reactors (not shown).

Referring still to FIG. 5, in the preferred embodiment, lower end of 108 of passage 104 has a greater cross sectional area than upper end 106 of passage 104. That is, a transverse cross section taken through passage 104 adjacent outlet 112 has a greater cross sectional area than a transverse section taken through passage 104 adjacent inlet 110. For example, the cross sectional area taken adjacent outlet 112 may have an area of between about 40 ft$^2$ and about 60 ft$^2$ and the cross sectional area taken adjacent inlet 110 may have an area of between about 20 ft$^2$ and about 40 ft$^2$.

Sidewalls 102 may be configured in a variety of ways in order to provide lower end 108 with a greater cross sectional area than upper end 106. In the embodiment shown, sidewall 102a and sidewall 102b are opposed to each other, and sidewall 102c and sidewall 102d are opposed to each other, and each of the sidewalls diverge from axis 105 going from inlet 110 to outlet 112. Accordingly, passage 104 is substantially frusto-pyramidal, and lower end 108 has a greater cross sectional area than upper end 106. In an alternate embodiment, sidewalls 102a and 102b may extend substantially parallel to axis 105, and sidewalls 102c and 102d may diverge from axis 105. In yet another alternate embodiment, holding tank apparatus 100 may comprise a single rounded sidewall defining a frustoconical passage 104. In yet another embodiment, sidewalls 102 may be stepped. It is preferred that sidewalls 102 continually diverge and that they continually diverge for the entire length of passage 104 as exemplified. Preferably, they diverge at an angle A from the vertical from about 1° to about 20°, preferably from about 2° to about 5°. It will also be appreciated that inner surface 138 of sidewalls 102 are preferably smooth and clear of projections that could be a source causing bridging to occur.

Providing lower portion 108 with a greater cross sectional area than upper portion 106 may aid in preventing cellulosic material from adhering or sticking to sidewalls 102 as the cellulosic material passes through holding tank apparatus 100. Accordingly, each portion of cellulosic feedstock that passes through holding tank apparatus 100 may have essentially the same residence time in passage 104.

In alternate embodiments, lower portion 108 of passage 104 may not have a greater cross sectional area than upper portion 106 of volume 104. For example, each of sidewalls 102 may extend essentially vertically and parallel to each other.

In some embodiments, the feedstock may travel directly downwardly to the next process unit, e.g. a steam explosion reactor. In such a case, it is preferred the passage continually increase in cross sectional area (as opposed to using a hopper). However, it is preferred that the feedstock, after traveling downwardly through passage 104, is conveyed laterally (transverse to axis 105). Further, it is preferred that the feedstock is actively withdrawn from holding tank 104 instead of permitting the feedstock to passively exit therefrom. Accordingly holding tank 100 may further comprise or be provided with at least one conveyor adjacent outlet 112 that is configured to actively convey the cellulosic feedstock laterally across outlet 112 to withdraw the cellulosic feedstock from passage 104. Referring to FIGS. 5 to 8, in the embodiment shown, the at least one conveyor comprises a plurality of screw conveyors 126, which are housed in a housing 116. The conveyor may be any transport mechanism known in the art to actively transport feedstock laterally from outlet 112. For example, the conveyor may comprise an auger, a screw conveyor, tabbed flight screw with bars, or the like that extends transversely to axis 105.

In the embodiment shown, housing 116 comprises a base 118, sidewalls 120, and an open top 122. Open top 122 is preferably at least as large as outlet 112, and is in vertical registration with outlet 112, such that material passing through outlet 112 may pass directly downwardly through open top 122. It will be appreciated that in alternate embodiments, sidewalls 102 of passage 104 may provide the sidewalls of housing 116. That is, sidewalls 102 may extend beyond outlet 112. Accordingly, in such an embodiment, outlet 112 of passage 104 may not be defined by ends 114 of sidewalls 102, and rather, may be defined by a portion of sidewalls 102 above ends 114.

Housing 116 comprises at least a first housing outlet 124, through which cellulosic feedstock conveyed by screw conveyors 126 exits housing 116. Cellulosic feedstock exiting housing outlet(s) 124 may pass into one or more conduits 125, which may, for example, lead to one or more, e.g., autohydrolysis reactors (not shown). Preferably each conduit 125 is provided with one or more screw conveyors or the like extending in the direction of conduit 125. Preferably more than one outlet 124 is provided. An advantage of having more then one outlet is that two treated feedstock streams may be provided from holding tank 100, each of which may be fed to a different downstream process vessel, e.g. a different steam explosion reactor.

Figure 6:
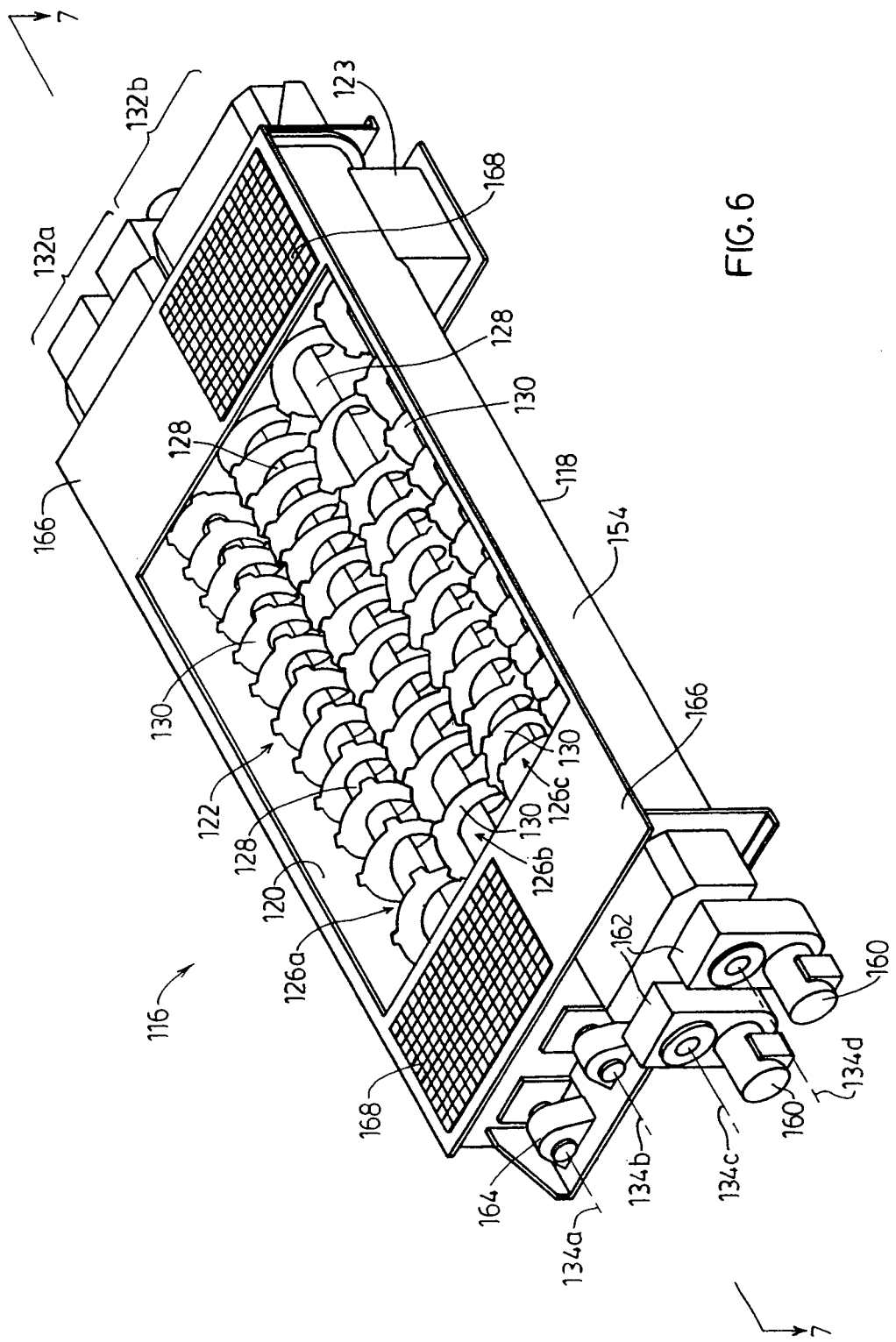
FIG. 6 is a perspective view of an embodiment of discharge member of the present invention, shown removed from a holding tank.
Figure 7:
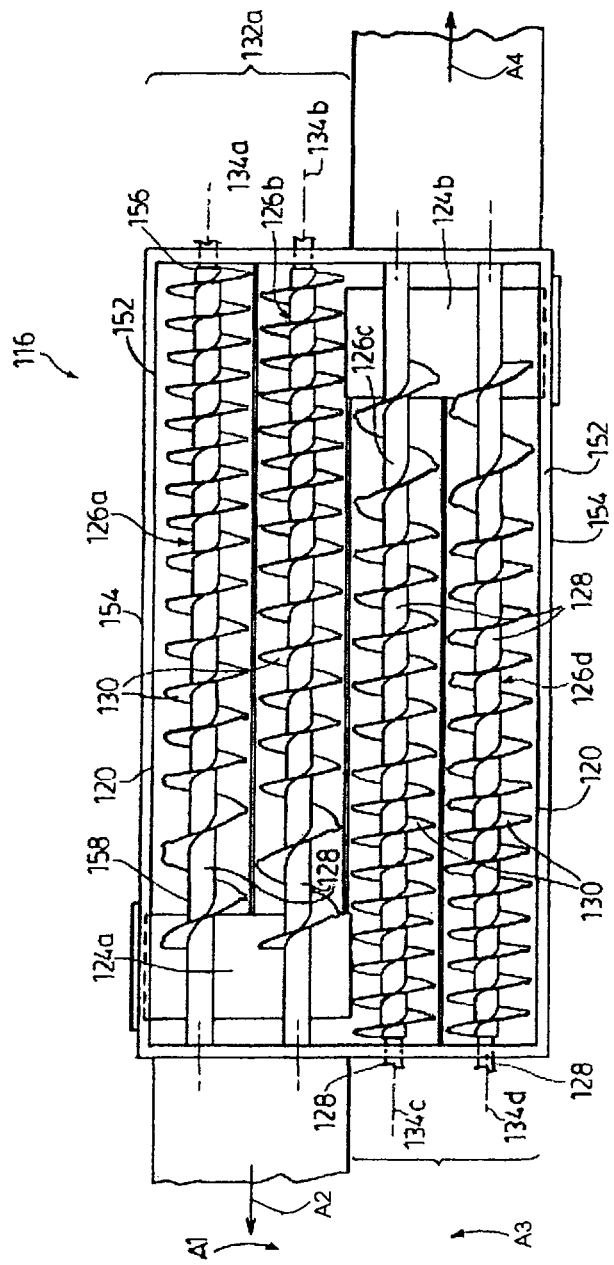
FIG. 7 is a cross-section taken along line 7-7 in FIG. 6.
Figure 8:
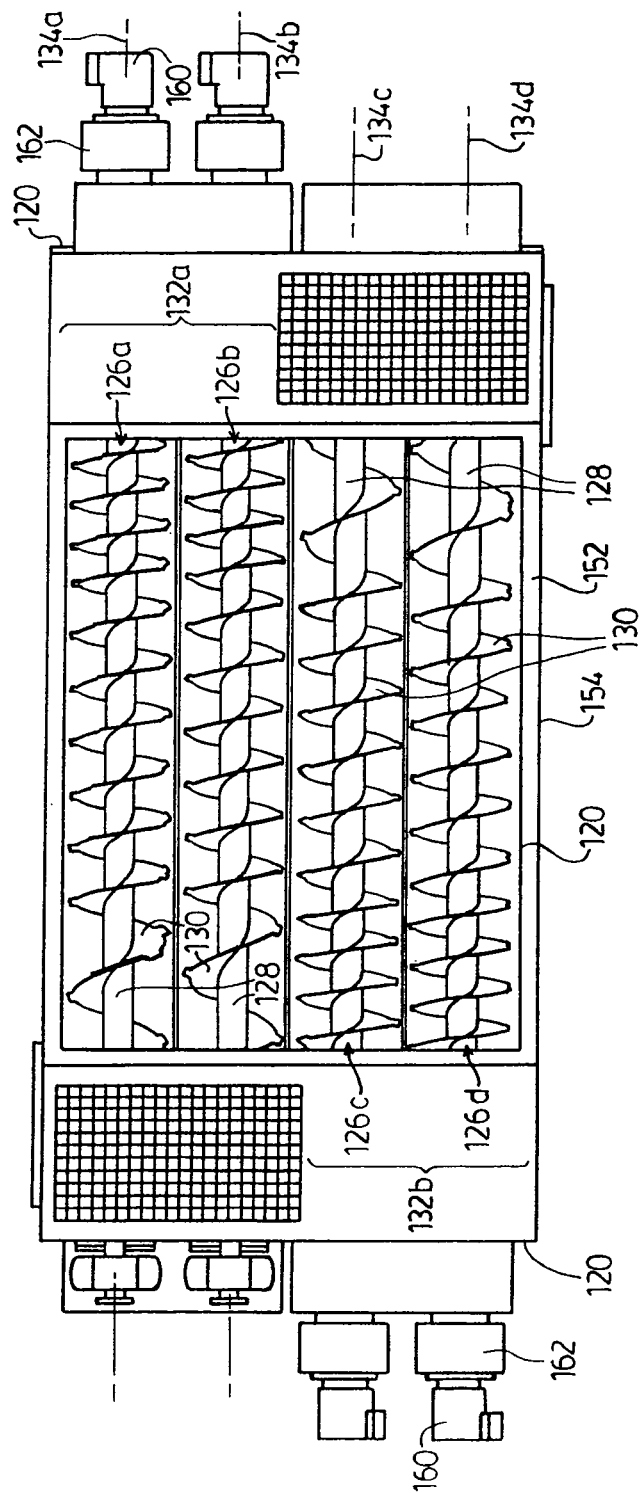
FIG. 8 is a top view of the discharge member of FIG. 6.
Figure 9:
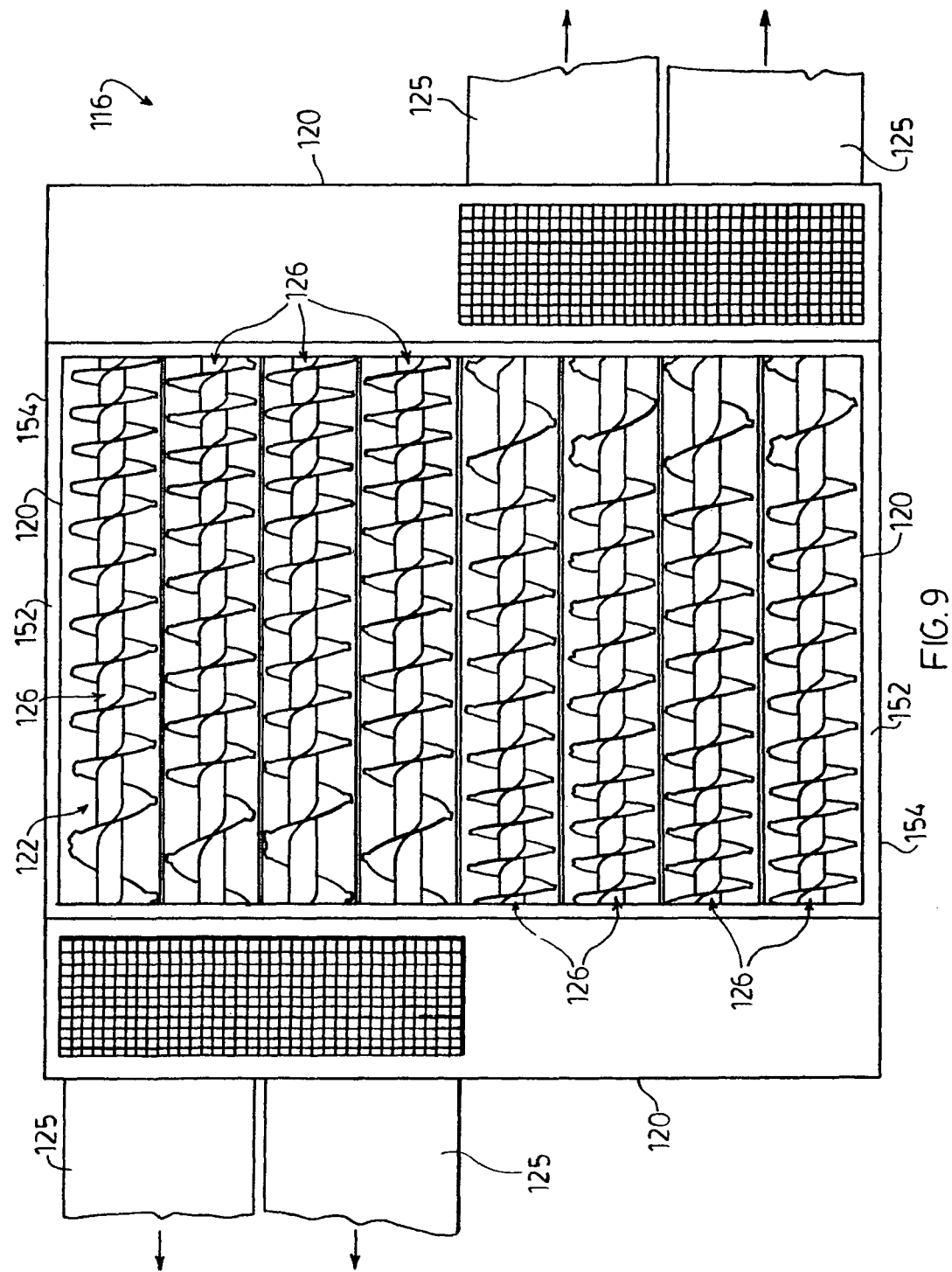
FIG. 9 is a top view of an alternate embodiment of a discharge member of the present invention; and, FIG. 10 is a cross-section taken along line 10-10 in FIG. 1.

As exemplified, housing 116 comprises two housing outlets 124a, 124b, defined in base 118 (see FIG. 7). Preferably, each outlet 124 is positioned such that it is not underneath passage 104 (laterally spaced from passage 104) and preferably more then one outlet 124 is provided. An advantage of positioning outlets 124 laterally from passage 104 is that feedstock may be withdrawn from all of outlet 112 and, more preferably, evenly from across outlet 112. Further, housing outlets 124a and 124b are preferably positioned on opposite sides of housing 116. Accordingly, housing outlets 124a and 124b may direct cellulosic material to two different, e.g., autohydrolysis reactors, positioned on opposite sides of holding tank 100. As exemplified in FIGS. 1 and 6, housing 116 may have upper wall 166 that extends over the portion of housing 116 positioned laterally of holding tank 100. Top wall 166 may cover the portion of screw conveyor 126 positioned laterally of holding tank 100. Optionally, a grate 168, or other member that provides a window, may be position in top wall 166 above outlet 124. Grate 168 permits a worker to observe the travel of feedstock into conduits 125.

As exemplified the screw conveyors 126 are mounted above base 118, and each screw conveyor extends transversely to axis 105 across all of outlet 112 (i.e. the length L of each screw conveyor extends at least from a first side of outlet 112 to a second side of outlet 112). Each screw conveyor 126 comprises a shaft 128 and at least one helical flight 130 extending about the shaft, and is configured to rotate to engage material exiting outlet 112, and to convey it towards one of the housing outlets 124. Shaft 128 may be rotatably mounted by any means known in the art. As exemplified, shaft 128 has one end journalled in a bearing housing 164 and a second end journalled in a transmission housing 162.

In the embodiment shown, housing 116 comprises four screw conveyors 126, which are arranged in pairs. Each pair comprises two adjacent screw conveyors 126 which convey the cellulosic feedstock in the same direction towards a common housing outlet 124. In the embodiment shown, first pair 132a comprises screw conveyors 126a and 126b, which rotate about respective first 134a and second 134b generally parallel axes, and second pair 132b comprises screw conveyors 126c, and 126d, which rotate about respective first 134c and second 134d generally parallel axes. Each of axes 134 are preferably horizontal, but may be at an angle of up to 45° or greater from the horizontal. Accordingly, screw conveyors 126a and 126b transport treated feedstock to outlet 124a and screw conveyors 126c and 126d transport treated feedstock to outlet 124b, which is on an opposed side to outlet 124a. It will be appreciated that screw conveyors 126a, 126b, 126c and 126d extend under essentially all of outlet 112. Therefore, the screw conveyors 126 preferably withdraw treated feedstock for all portions of outlet 112. Alternately, or in addition, each outlet 124 may have one or more screw conveyors 126 or other transport member associated therewith.

Referring still to FIG. 7, as exemplified, screw conveyors 126a and 126b of first pair 132a may each be rotated in a direction indicated by arrow A1, to feed material from above in a direction indicated by arrow A2 towards housing outlet 124a. Further, screw conveyors 126c and 126d of second pair 132b may each be rotated in a direction indicated by arrow A3, to feed material from above in a direction indicated by arrow A4 towards housing outlet 124b.

In order to permit each screw conveyors 126 to be rotated in a particular direction of rotation, each screw conveyor may be driven by its own drive motor 160. As shown in FIGS. 6 and 7, each shaft 128 extends outwardly past sidewall 120 into a transmission housing 162 wherein motor 160 is drivingly connected to shaft 128. Any driving linkage known in the art may be used. It will be appreciated that in an alternate embodiment, two or more shafts may be driven by a single motor 160.

Accordingly, as exemplified, housing outlets 124a and 124b are positioned on laterally opposite sides of housing 116, and each helical flight 130 is right-handed. Accordingly, direction A1 and direction A3 are opposite to each other, and directions A2 and A4 are opposite to each other. However, in alternate embodiments, housing outlets 124a and 124b may be positioned on the same lateral side as each other. In such an embodiment, directions A1 and A3 may be substantially the same, and directions A2 and A4 may be substantially the same. In yet further alternate embodiments, the helical flight 130 of the first pair 132a of screw conveyors 126a, 126b, may be right handed, and the helical flight 130 of the second pair 132b of screw conveyors 126c, 126d may be left handed. Accordingly, in such an embodiment, directions A1 and A3 may be the same, and direction A2 and A4 may be opposite. It will be appreciated that each pair of screw conveyors 126 may be configured such that they rotate in opposite directions. For example, screw conveyor 126a may be configured to rotate clockwise and screw conveyor 126b may be configured to rotate counterclockwise.

It will be appreciated that in alternate embodiments, one or more screw conveyors 126 may be otherwise configured. For example, housing 116 may comprise only one screw conveyor 126 and one outlet 124, or housing 116 may comprise a plurality of screw conveyors which are not arranged in pairs (e.g the screw conveyors may be arranged in sets of three, or as single screw conveyors), or housing 116 may comprise more than two pairs of screw conveyors. For example, in an alternate embodiment shown in FIG. 9, holding tank 100 comprises four housing outlets 124, and four pairs 132 of screw conveyors 126.

Referring still to FIGS. 5-7, at least one of the screw conveyors 126, and preferably all of the screw conveyors 126, has a variable pitch along its length. That is, the pitch of helical flight 130 is not constant along the length L of at least one of the screw conveyors 126.

For example, in the embodiments shown, each screw conveyor has a first end 158 proximal to its respective housing outlet 124 (i.e. the housing outlet towards which it conveys cellulosic feedstock), and a second end 156 distal to its respective housing outlet 124 (shown in FIG. 7). The pitch of helical flight 130 at first end 158 is greater or wider than the pitch of helical flight 130 at second end 156. For example, the pitch at the first end may be between about 14 inches and about 18 inches, and the pitch at the second end may be between about 4 inches and about 8 inches.

In the embodiments shown, the pitch of each helical flight 130 varies at a constant rate between the first end 158 and the second end 156. That is, the pitch gradually becomes wider towards each discharge member outlet 124. In alternate embodiments, an abrupt transition between wider and narrower regions of flight may occur. For example, each screw conveyor may have a first region extending from first end 158 towards a mid-point of screw conveyor 126, and a second region extending from second end 156 towards the midpoint. The first region may have a first range of pitch and the second region has a second range of pitch. For example, the first range of pitch may be between about 14 inches and about 18 inches, and the second range of pitch may be between about 4 inches and about 8 inches. In yet another embodiment, each screw conveyor may comprise an intermediate region between the first region and the second region, and the intermediate region may have a third range of pitch that is less than the first range of pitch and more than the second range of pitch. For example, the third range of pitch may be between about 6 inches and about 10 inches.

Preferably, the screw conveyors 126 of each pair 132 have the same pitch at any location along their lengths. That is, the helical flight of screw conveyors 126a and 126b is essentially identical, and the helical flight of screw conveyors 126c and 126d is essentially identical.

Furthermore, the pitch of a first pair of screw conveyors is preferably a mirror image of the pitch of a second pair of screw conveyors, which convey the cellulosic feedstock in a direction opposite to the first pair of screw conveyors. That is, the pitch of screw conveyors 126a and 126b, which convey cellulosic material in direction A2, is a mirror image of the pitch of screw conveyors 126c and 126d, which convey cellulosic material in a direction A4.

Providing each screw conveyor with a variable pitch, and more specifically with a narrower pitch distal to the housing outlet, permits more equal amounts, and may allow for substantially equal amounts of cellulosic feedstock to be withdrawn from each portion of outlet 112. That is, material deposited in screw conveyor 126 at the distal end 156 will be conveyed towards the respective outlet 124 for that screw conveyor. As that material is transported laterally, the pitch of the screw increases permitting additional material to be deposited directly in the screw conveyor from outlet 112. Further increases in the pitch will permit additional portions of the material to fall into screw conveyor. The portion or portions of the screw conveyor closer to outlet 124 (in the direction of transport) has a wider pitch such that it may accommodate material conveyed from the distal region, as well as material deposited directly thereon from passage 104. Accordingly, feedstock is withdrawn from across all of outlet 112.

Referring to FIGS. 5 and 10, holding tank apparatus 100 preferably further comprises a heating jacket 136 provided on at least a portion of the holding tank apparatus 100. Preferably, the at least one sidewall 102 is provided with a heating jacket. For example, in the embodiment shown, heating jacket 136 surrounds all of each sidewall 102. Heating jacket 136 may comprise a plurality of outer walls that are generally parallel to and spaced from sidewalls 102 so as to define an enclosure 142 therebetween. A fluid may be passed through enclosure 142 from an inlet (not shown) to an outlet (not shown) so that a heated fluid is passed through enclosure 142. Heating jacket 136 may be of any construction known in the art. Accordingly, the cellulosic material may be heated to a predetermined temperature, or maintained at a predetermined temperature as it passes through holding tank apparatus 100.

Referring to FIG. 5, in a further preferred embodiment, housing 116 also comprises a second heating jacket 146 provided by housing 116. In the embodiment shown, heating jacket 146 is configured similarly to heating jacket 136, and may comprise an outer wall 154 spaced outwardly from sidewalls 120 and/or base 118 and is configured for passing a heated fluid through an enclosure 150 defined between outer walls 154 and sidewalls 120 and/or base 118. Heating jacket 146 may be of any construction known in the art.

In some embodiments, one or more temperature sensors may be provided in passage 104. For example, a first thermocouple (not shown) may be provided in the upper portion 106 of passage 104, to measure the temperature of the cellulosic feedstock entering inlet 110, and a second thermocouple (not shown) may be provided in the lower portion 108 of passage 104, to measure the temperature of the cellulosic feedstock exiting outlet 112. In some embodiments, one or more displays (not shown) may be coupled to the one or more temperature sensors, such that a user may view the measured temperatures, and optionally, adjust the amount of heat provided to holding tank 100 based on the measured temperatures. In further embodiments, the one or more sensors may be coupled to a processor, which may automatically adjust the amount of heat provided to holding tank 100 based on the measured temperatures.

A method of treating a cellulosic feedstock that may be used for ethanol production will now be described. Although the method will be described with reference to holding tank apparatus 100, it will be appreciated that the method may be carried out using an alternate apparatus, and holding tank apparatus 100 may be operated according to an alternate method.

A suitable cellulosic feedstock is preferably first subjected to moisture impregnation to raise the moisture content of the feedstock to a predetermined level prior to entry to the holding tank. Preferably, the moisture content of the feedstock upon entry to the holding tank is from about 30 wt % to about 60 wt %, preferably from about 45 wt % to about 55 wt %. The cellulosic feedstock may be obtained from, for example, a pre-treatment device such as impregnator 10, in which moisture is added to the cellulosic feedstock to raise the moisture content from, e.g., less than about 15% to between about 30% and about 60 wt % upon entry to the holding tank. Preferably, the moisture content is between about 45 wt % and about 55 wt % upon entry to the holding tank.

In a water impregnator, water is added to the feedstock. Preferably, the amount that is added is sufficient to raise the moisture level to a predetermined level for the downstream process, preferably hydrolysis, more preferably autohydrolysis followed by enzymatic hydrolysis. In order to prevent excess water being added to the feedstock, a limited amount of water is preferably provided such that excess water need not be removed. As the feedstock is fibrous and comprises discrete blocks of material, the mass transfer characteristics of the material govern the rate at which moisture applied to the outside of the feedstock penetrates into the core of the feedstock such that the moisture level taken across each block of material is generally uniform. Autohydrolysis in a steam explosion reactor is a relatively quick process (the residence time may be from about 2 to about 10 minutes). Due to the short residence time, it has been determined that some (e.g., the inner core of the blocks of material) may not be fully reacted during autohydrolysis if those portions do not have a sufficient moisture content. This incomplete reaction may require either separation of the unreacted material prior to downstream processing (e.g., hydrolysis) or permitting unreacted material to pass through the downstream process units, which may result in material not converted to fermentable sugars.

It has also been determined that heating the feedstock above about 70° C. results in degradation of the sugars in the feedstock. If the feedstock is over heated, then portions of the hemicellulose will degrade resulting in loss of yield and potential negative effect on subsequent enzymatic hydrolysis or fermentation process. Further, if the material that enters an autohydrolysis reactor is too cold, then the first portion of the reactor will tend to act as a preheater rather than as a autohydrolysis reaction resulting in a reduced yield.

Accordingly, the cellulosic feedstock, preferably after being subjected to impregnation, is then conveyed to a holding tank wherein the feedstock is passed through a heated passage. The heated holding tank may be, for example, holding tank 100, which comprises an inlet 110 disposed at an elevation above outlet 112. Accordingly, the cellulosic feedstock may be passed downwardly through the holding tank from the inlet towards the outlet under the force of gravity.

The feedstock is preferably provided with a residence time in the holding tank such that a desired moisture and temperature profile through the material is obtained. For example, it is preferred that the core of the blocks of material have a moisture content that is within 80%, preferably 90% of the moisture content of the exterior surface of the material. Accordingly, for example, if the moisture content of the exterior surface of the material is from 45 wt % to 55 wt %, then the moisture content of the core of the material is preferably from 40.5 to 49.5 wt %.

The holding tank may be heated in a variety of ways, for example by passing a heated fluid through a heating jacket provided on at least a portion of the holding tank. The heating jacket may be, for example, heating jacket 136 and optionally heating jacket 146. Optionally, electrical resistance heating may be used. Heat may also be supplied internally in passage 104.

The heated holding tank preferably serves to maintain the cellulosic feedstock at a desired temperature. For example, in some embodiments, the cellulosic feedstock enters the holding tank at a temperature of between about 50° C. and about 70° C., preferably between about 50° C. and about 65° C., and the holding tank is configured to maintain the cellulosic feedstock at the temperature between about 50° C. and about 70° C., and preferably between about 50° C. and about 65° C. In alternate embodiments, rather than maintaining the cellulosic feedstock at a desired temperature, the heated holding tank may serve to heat the cellulosic feedstock to a desired temperature. For example the cellulosic feedstock may enter the heated holding tank at a first temperature, and may exit the holding tank at a second temperature higher than the first temperature. The second temperature may be, for example, between about 50° C. and about 70° C., and more preferably, between about 55° C. and about 65° C.

Preferably, a heated fluid is used to heat the feedstock. The fluid preferably has a temperature from 70 to 90° C. In order to avoid overheating the feedstock and degrading the sugars in the feedstock, the upper temperature of the heat source is limited requiring a consequential increase in the residence time (e.g., up to one hour) prior to subjecting the feedstock to downstream processing, preferably autohydrolysis, so that the core of the blocks may be raised to a predetermined temperature. For example, it is preferred that the core of the blocks of material have a temperature that is within 80%, preferably 90% of the temperature of the exterior surface of the material. Accordingly, for example, if the temperature of the exterior surface of the material is from 50 to 70° C., then the temperature of the core of the material is preferably from 45 to 63° C.

In some embodiments, the method may further comprise monitoring the temperature of the cellulosic feedstock in the heated holding tank. For example, as described previously, one or more temperature sensors may be provided within the holding tank. Preferably, a first temperature sensor is provided adjacent to the inlet of the holding tank, and a second temperature sensor is provided at the outlet of the holding tank. In further embodiments, the method may further comprise adjusting the amount of heat applied to the holding tank based on the temperature of the cellulosic material in the holding tank. For example, in some embodiments, it may be desired that the temperature of the cellulosic feedstock exiting the heated holding tank is about 65° C. Accordingly, in such an embodiment, if the first temperature sensor reads a temperature of about 55° C., for example, and the second temperature sensor reads a temperature of about 60° C., for example, the amount of heat applied to the holding tank may be increased until the second temperature sensor reads a temperature of 65° C. The amount of heat may be increased by, for example, increasing a flow rate of the fluid circulating in the heating jacket, or by increasing a temperature of the fluid circulating in the heating jacket. Preferably, the amount of heat applied is adjusted automatically, for example by a processor coupled to the temperature sensors and to the heating jacket. Alternatively, the amount of heat applied may be adjusted manually.

The cellulosic feedstock is preferably withdrawn in a lateral direction from the holding tank and, more preferably, with generally even amounts withdrawn from all portions of the outlet of the holding tank. By withdrawing from all portions of the outlet of the holding tank, each layer of feedstock entering the holding tank may have a generally uniform residence time in the holding tank.

The cellulosic feedstock is preferably subsequently subjected to hydrolysis. More preferably, the cellulosic feedstock is subjected to autohydrolysis followed enzymatic hydrolysis, converting the cellulose of the cellulosic feedstock to one or more sugars. The hydrolysis may take place in one or more hydrolysis reactors, which may include autohydrolysis (not shown), which are provided downstream from the holding tank, and are in fluid communication with the holding tank. For example, as described hereinabove, one or more conduits 125 may extend from housing outlets 124 towards one or more autohydrolysis reactors.

The method is preferably carried out such that the cellulosic feedstock has a residence time in the holding tank of up to 60 minutes. The feedstock may have a residence time in the holding tank of between about 5 minutes and about 45 minutes and preferably between 10 minutes and 30 minutes.

Furthermore, the method is preferably operated continuously and at steady state, such that the rate at which cellulosic feedstock is deposited into an inlet of the holding tank is equal to the rate at which cellulosic feedstock is removed from the outlet of the holding tank. Accordingly, in use, the method is preferably preceded by an initial start up phase, wherein material is not removed from the holding tank, and the tank is filled with cellulosic feedstock from impregnation chamber 12. When the tank is filled to a desired level, the method may commence, such that the holding tank is operated at steady state, and a generally constant residence time is maintained.

It will be appreciated that certain features of the invention, which are, for clarity, described in the context of separate embodiments or separate aspects, may also be provided in combination in a single embodiment. Conversely, various features of the invention, which are, for brevity, described in the context of a single embodiment or aspect, may also be provided separately or in any suitable sub-combination.

Although the invention has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

We claim:

1. A method for preparing a cellulosic feedstock comprising:
   (a) obtaining a cellulosic feedstock having a moisture content of 30 wt % and 60 wt %;

(b) passing the moistened cellulosic feedstock through a heated holding tank, the heated holding tank comprising (i) at least one sidewall defining a passage having an upper portion and a lower portion, (ii) at least one inlet adjacent to the upper portion, and (iii) at least one outlet adjacent the lower portion, wherein the holding tank has a longitudinal axis and at least one of the at least one sidewalls diverges from the longitudinal axis from the upper portion to the lower portion;

(c) withdrawing the cellulosic feedstock from the at least one outlet of the heated holding tank; and, (d) subsequently subjecting the cellulosic feedstock to hydrolysis.

2. The method of claim 1, wherein the moisture content of the moistened cellulosic feedstock is between 45 wt % and 55 wt %.

3. The method of claim 1, wherein step (b) comprises passing the moistened cellulosic feedstock downwardly through the heated holding tank.

4. The method of claim 3, wherein the moistened cellulosic feedstock is passed downwardly through the heated holding tank under the force of gravity.

5. The method of claim 1, wherein the moistened cellulosic feedstock has a residence time of up to 60 minutes in the heated holding tank.

6. The method of claim 1, wherein the moistened cellulosic feedstock has a residence time of between 5 minutes and 45 minutes in the heated holding tank.

7. The method of claim 1, wherein moistened cellulosic feedstock has a residence time of between 10 minutes and 30 minutes in the heated holding tank.

8. The method of claim 1, wherein the heated holding tank is heated by passing a heated fluid through a heating jacket provided on at least a portion of the heated holding tank.

9. The method of claim 1, wherein the moistened cellulosic feedstock enters the heated holding tank at a temperature of between 50° C. and 70° C.

10. The method of claim 1, wherein the moistened cellulosic feedstock enters the heated holding tank at a temperature between 50° C. and 65° C.

11. The method of claim 1, further comprising maintaining the moistened cellulosic feedstock at a temperature of between 50° C. and 70° C. while in the heated holding tank.

12. The method of claim 1, wherein the moistened cellulosic feedstock enters the heated holding tank at a first temperature, and exits the heated holding tank at a second temperature higher than the first temperature.

13. The method of claim 12, wherein the first temperature is below 50° C., and the second temperature is between 50° C. and 70° C.

14. The method of claim 1, wherein step c) comprises withdrawing cellulosic feedstock from essentially the entirety of the at least one outlet.

15. The method of claim 1, further comprising monitoring a temperature of the moistened cellulosic material in the heated holding tank.

16. The method of claim 15, further comprising adjusting an amount of heat applied to the heated holding tank based on the temperature of the cellulosic material in the heated holding tank.

17. The method of claim 1, further comprising conveying the cellulosic feedstock through a water impregnator wherein water is added to increase the moisture content of the cellulosic feedstock from less than 15 wt % to 30 wt % to 60 wt %.

18. The method of claim 1, wherein the hydrolysis comprises the use of a steam explosion reactor.

19. A method for preparing a cellulosic feedstock comprising:

(a) treating a starting cellulosic feedstock in an impregnator with water and obtaining a moistened cellulosic feedstock;

(b) passing the moistened cellulosic feedstock through a heated holding tank, the heated holding tank comprising (i) at least one sidewall defining a passage having an upper portion and a lower portion, (ii) at least one inlet adjacent to the upper portion, and (iii) at least one outlet adjacent the lower portion, wherein the holding tank has a longitudinal axis and at least one of the at least one sidewalls diverges from the longitudinal axis from the upper portion to the lower portion;

(c) withdrawing heated moistened cellulosic feedstock from the at least one outlet of the heated holding tank, wherein the cellulosic feedstock is maintained at a temperature of between 50° C. and 70° C. while in the heated holding tank; and, (d) subsequently conveying the cellulosic feedstock to a steam explosion reactor.

20. The method of claim 19, wherein the moisture content of the cellulosic feedstock is increased from less than 15 wt % to 30 wt % to 60 wt % in the impregnator.

21. The method of claim 19, wherein the moisture content is between 45 wt % and 55 wt%.

22. The method of claim 19, wherein step (b) comprises passing the cellulosic feedstock downwardly through the heated holding tank.

* * * * *